United States Patent
Khader et al.

(10) Patent No.: US 11,642,405 B2
(45) Date of Patent: May 9, 2023

(54) NANOEMULSION AND METHODS OF USE THEREOF

(71) Applicant: Washington University, St. Louis, MO (US)

(72) Inventors: Shabaana Abdul Khader, St. Louis, MO (US); Mushtaq Ahmed, St. Louis, MO (US); Ali Fattom, St. Louis, MO (US); Douglas Smith, St. Louis, MO (US); Tarek Hamouda, St. Louis, MO (US)

(73) Assignees: Washington University, St. Louis, MO (US); BLUEWILLOW BIOLOGICS, Ann Arbor, MI (US)

( * ) Notice: Subject to any disclaimer, the term of this patent is extended or adjusted under 35 U.S.C. 154(b) by 0 days.

(21) Appl. No.: 16/624,722

(22) PCT Filed: Jun. 19, 2018

(86) PCT No.: PCT/US2018/038296
§ 371 (c)(1),
(2) Date: Dec. 19, 2019

(87) PCT Pub. No.: WO2018/236876
PCT Pub. Date: Dec. 27, 2018

(65) Prior Publication Data
US 2020/0113990 A1   Apr. 16, 2020

Related U.S. Application Data

(60) Provisional application No. 62/530,548, filed on Jul. 10, 2017, provisional application No. 62/521,938, filed on Jun. 19, 2017.

(51) Int. Cl.
*A61K 39/04*     (2006.01)
*G01N 33/50*     (2006.01)
*A61K 39/00*     (2006.01)

(52) U.S. Cl.
CPC .......... *A61K 39/04* (2013.01); *G01N 33/505* (2013.01); *A61K 2039/5154* (2013.01); *A61K 2039/543* (2013.01); *A61K 2039/55566* (2013.01)

(58) Field of Classification Search
CPC ..................................................... A61K 39/04
See application file for complete search history.

(56) References Cited

U.S. PATENT DOCUMENTS

| 6,406,705 B1 | 6/2002 | Davis et al. | |
| 2006/0251684 A1* | 11/2006 | Annis | A61K 31/7048 424/400 |
| 2008/0317799 A1* | 12/2008 | Baker | A61K 31/198 424/405 |
| 2011/0027349 A1* | 2/2011 | Sable | A61K 39/04 424/450 |
| 2012/0328701 A1* | 12/2012 | Edelson | A61P 25/02 424/490 |

FOREIGN PATENT DOCUMENTS

WO    2018236876 A2    12/2018

OTHER PUBLICATIONS

'Report on BCG vaccine use for protection against mycobacterial infections including tuberculosis, leprosy, and other nontuberculous mycobacteria infections', BCG vaccines, 2017 pp. 1-10. (Year: 2017).*
Aagaard et al., A multistage tuberculosis vaccine that confers efficient protection before and after exposure, Nature Medicine, 2011; pp. 1-7 (Year: 2011).*
Martin, Eur Respir J, 2005; 26(1):162-167 (Year: 2005).*
Monin, L. et al., "Immune requirements for protective Th17 recall responses to *Mycobacterium tuberculosis* challenge," Mucosal Immunol., Sep. 2015, pp. 1099-1109, vol. 8, No. 5.
Mutsch, M. et al., "Use of the Inactivated Intranasal Influenza Vaccine and the Risk of Bell's Palsy in Switzerland," N. Engl. J. Med., 2004, pp. 896-903, vol. 350.
Nakae, S. et al., "Antigen-Specific T Cell Sensitization is Impaired in IL-17-Deficient Mice, Causing Suppression of Allergic Cellular and Humoral Responses," Immunity, Sep. 2002, pp. 375-387, vol. 17, Cell Press.
Ndiaye, B. et al., "Safety, immunogenicity, and efficacy of the candidate tuberculosis vaccine MVA85A in healthy adults infected with HIV-1: a randomised, placebo-controlled, phase 2 trial," Lancet Respir. Med., 2015, pp. 190-200, vol. 3.
Neutra, M. et al., "Mucosal vaccines: the promise and the challenge," Nat. Rev. Immunol., Feb. 2006, pp. 148-158, vol. 6, Nature Publishing Group.
Priebe, G. et al., "IL-17 is a Critical Component of Vaccine-Induced Protection against Lung Infection by Lipopolysaccharide-Heterologous Strains of Pseudomonas aeruginosa," J. Immunol., 2008, pp. 4965-4975, vol. 181.
Rangel-Moreno, J. et al., "Pulmonary expression of CXC chemokine ligand 13, CC chemokine ligand 19, and CC chemokine ligand 21 is essential for local immunity to influenza," PNAS, Jun. 2007, pp. 10577-10582, vol. 104, No. 25.
Rangel-Moreno, J. et al., "The development of inducible Bronchus-Associated Lymphoid Tissue (iBALT) is dependent on IL-17," HHS Public Access Author Manuscript, Dec. 12, 2012, pp. 1-25, published in final edited form as: Nat. Immunol., 2011, pp. 639-646, vol. 12, No. 7.
Reiley, W. et al., "ESAT-6-specific CD4 T cell responses to aerosol *Mycobacterium tuberculosis* infection are initiated in the mediastinal lymph nodes," PNAS, Aug. 2008, pp. 10961-10966, vol. 105, No. 31.

(Continued)

*Primary Examiner* — Brian Gangle
*Assistant Examiner* — Lakia J Jackson-Tongue
(74) *Attorney, Agent, or Firm* — Polsinelli PC

(57) ABSTRACT

The present disclosure relates to compositions and methods for inducing an immune response to a composition of the invention in a subject. Additionally, the present disclosure generally relates to methods for screening for immune response to a composition of the invention.

17 Claims, 14 Drawing Sheets
(4 of 14 Drawing Sheet(s) Filed in Color)
Specification includes a Sequence Listing.

(56) References Cited

OTHER PUBLICATIONS

Rook, G. et al., "Immune responses to tuberculosis in developing countries: implications for new vaccines," Nat. Rev. Immunol., Aug. 2005, pp. 661-667, vol. 5.
Santosuosso, M. et al., "Mechanisms of Mucosal and Parenteral Tuberculosis Vaccinations: Adenoviral-Based Mucosal Immunization Preferentially Elicits Sustained Accumulation of Immune Protective CD4 and CD8 T Cells within the Airway Lumen," J. Immunol., 2005, pp. 7986-7994, vol. 174.
Saunders, B. et al., "Restraining mycobacteria: Role of granulomas in mycobacterial infections," Immunol. Cell Biol., 2000, pp. 334-341, vol. 78.
Slight, S. et al., "CXCR5(+) T helper cells mediate protective immunity against tuberculosis," J. Clin. Invest., 2013, pp. 712-726, vol. 123, No. 2.
Stanberry, L. et al., "Safety and immunogenicity of a novel nanoemulsion mucosal adjuvant W805EC combined with approved seasonal influenza antigens," Vaccine, 2012, pp. 307-316, vol. 30.
Sweeney, K. et al., "A recombinant Mycobacterium smegmatis induces potent bactericidal immunity against *Mycobacterium tuberculosis*," NIH Public Access Author Manuscript, Jan. 3, 2012, pp. 1-18, published in final edited form as: Nat. Med., 2011, pp. 1261-1268, vol. 17, No. 10.
Tameris, M. et al., "Safety and efficacy of MVA85A, a new tuberculosis vaccine, in infants previously vaccinated with BCG: a randomised, placebo-controlled phase 2b trial," Lancet, Mar. 23-29, 2013, pp. 1021-1028, vol. 381, No. 9871.
Tameris, M. et al., "The Candidate TB Vaccine, MVA85A, Induces Highly Durable Th1 Responses," PLoS One, Feb. 2014, pp. 1-12, vol. 9, No. 2, e87340.
Tchilian, E. et al., "Immunogenicity and Protective Efficacy of Prime-Boost Regimens with Recombinant (delta)ureChly+ *Mycobacterium bovis* BCG and Modified Vaccinia Virus Ankara Expressing *M. tuberculosis* Antigen 85A against Murine Tuberculosis," Infection and Immunity, Feb. 2009, pp. 622-631, vol. 77, No. 2.
Wang, J. et al., "Single Mucosal, but Not Parenteral, Immunization with Recombinant Adenoviral-Based Vaccine Provides Potent Protection from Pulmonary Tuberculosis," J. Immunol., 2004, pp. 6357-6365, vol. 173.
Wolf, A. et al., "Initiation of the adaptive immune response to *Mycobacterium tuberculosis* depends on antigen production in the local lymph node, not the lungs," J. Exp. Med., Jan. 2008, pp. 105-115, vol. 205, No. 1, The Rockefeller University Press.
Xing, Z. et al., "New Approaches to TB Vaccination," Chest, Sep. 2014, pp. 804-812, vol. 146, No. 3.
Zhang, Z. et al., "Cellular effectors mediating Th17-dependent clearance of pneumococcal colonization in mice," J. Clin. Invest., 2009, pp. 1899-1909, vol. 119, No. 7.
Zhang, C. et al., "*Mycobacterium tuberculosis* Secreted Proteins as Potential Biomarkers for the Diagnosis of Active Tuberculosis and Latent Tuberculosis Infection," J. Clin. Lab. Anal., 2015, pp. 375-382, vol. 29.
Aagaard, C. et al., "A multistage tuberculosis vaccine that confers efficient protection before and after exposure," Nature Med., 2011, pp. 189-194, vol. 17.
Aguilo, N. et al., "Pulmonary but Not Subcutaneous Delivery of BCG Vaccine Confers Protection to Tuberculosis-Susceptible Mice by an Interleukin 17-Dependent Mechanism," J. Infect. Dis., Mar. 2016, pp. 831-839, vol. 213.
Ahmed, M. et al., "Rationalized design of a mucosal vaccine protects against *Mycobacterium tuberculosis* challenge in mice," J. Leukoc. Biol., Jun. 2017, pp. 1373-1381, vol. 101.
Banus, S. et al., "The role of Toll-like receptor-4 in pertussis vaccine-induced immunity," BMC Immunol., 2008, pp. 1-15, vol. 9, No. 21.
Bertholet, S. et al., "A Defined Tuberculosis Vaccine Candidate Boosts BCG and Protects Against Multidrug-Resistant *Mycobacterium tuberculosis*," Sci. Transl. Med., Oct. 2010, pp. 1-10, vol. 2, No. 53, 53ra74.

Bielinska, A. et al., "Induction of Th17 Cellular Immunity With a Novel Nanoemulsion Adjuvant," NIJ Public Access Author Manuscript, Apr. 2010, pp. 1-16, published in final edited form as: Crit. Rev. Immunol., 2010, pp. 189-199, vol. 30, No. 2.
Carter, D. et al., "Role of Adjuvants in Modeling the Immune Response," NIH Public Access Author Manuscript, Jan. 2014, pp. 1-8, published in final edited form as: Curr. Opin. HIV. AIDS, Sep. 2010, pp. 409-413, vol. 5, No. 5.
Chatterjee, S. et al., "Early Secreted Antigen ESAT-6 of *Mycobacterium tuberculosis* Promotes Protective T Helper 17 Cell Responses in a Toll-Like Receptor-2-dependent Manner," PLoS Pathog., Nov. 2011, pp. 1-12, vol. 7, No. 11, e1002378.
Chen, L. et al., "Single Intranasal Mucosal *Mycobacterium bovis* BCG Vaccination Confers Improved Protection Compared to Subcutaneous Vaccination against Pulmonary Tuberculosis," Infect. Immun., Jan. 2004, pp. 238-246, vol. 71, No. 1.
Chen, K. et al., "Th17 Cells Mediate Clade-Specific, Serotype-Independent Mucosal Immunity," Immunity, Dec. 2011, pp. 997-1009, vol. 35.
Datta, S. et al., "Mucosal adjuvant activity of cholera toxin requires Th17 cells and protects against inhalation anthrax," PNAS, Jun. 2010, pp. 10638-10643, vol. 107, No. 23.
Dye, C. et al., "The Population Dynamics and Control of Tuberculosis," Sci., May 2010, pp. 856-861, vol. 328.
Dye, C., "The potential impact of new diagnostic tests on tuberculosis epidemics," Indian J. Med. Res., May 2012, pp. 737-744, vol. 135, No. 5.
El-Kamary, S. et al., "Adjuvanted intranasal Norwalk Virus-Like Particle Vaccine Elicits Antibodies and Antibody-Secreting Cells That Express Homing Receptors for Mucosal and Peripheral Lymphoid Tissues," J. Infect. Dis., Dec. 2010, pp. 1649-1658, vol. 202.
GenBank Accession No. A5U3Q3, dated Oct. 16, 2019, 3 pgs.
GenBank Accession No. AHN50412, dated Mar. 31, 2014, 1 page.
GenBank Accession No. AHN50413, dated Mar. 31, 2014, 1 page.
GenBank Accession No. CCE36540, dated Feb. 27, 2015, 2 pgs.
GenBank Accession No. CCE37859, dated Feb. 27, 2015, 1 page.
GenBank Accession No. CCE37920, dated Feb. 27, 2015, 2 pgs.
GenBank Accession No. CCP42850, dated Feb. 27, 2015, 2 pgs.
GenBank Accession No. CCP43952, dated Feb. 27, 2015, 2 pgs.
GenBank Accession No. CCP44499, dated Feb. 27, 2015, 2 pgs.
GenBank Accession No. CCP44804, dated Feb. 27, 2015, 2 pgs.
GenBank Accession No. CCP45424, dated Feb. 27, 2015, 2 pgs.
GenBank Accession No. CCP45426, dated Feb. 27, 2015, 2 pgs.
GenBank Accession No. CCP46229, dated Feb. 27, 2015, 2 pgs.
GenBank Accession No. P9WQN8, dated Oct. 16, 2019, 3 pgs.
GenBank Accession No. P9WQP3, dated Sep. 18, 2019, 7 pgs.
Goonetilleke, N. et al., "Enhanced Immunogenicity and Protective Efficacy Against *Mycobacterium tuberculosis* of Bacille Calmette-Guerin Vaccine Using Mucosal Administration and Boosting with a Recombinant Modified Vaccinia Virus Ankara," J. Immunol., 2003, pp. 1602-1609, vol. 171.
Gopal, R. et al., "IL-23-dependent IL-17 drives Th1-cell responses following *Mycobacterium bovis* BCG vaccination," Eur. J. Immunol., Feb. 2012, pp. 364-373, vol. 42, No. 2.
Gopal, R. et al., "Interleukin-17-dependent CXCL13 mediates mucosal vaccine-induced immunity against tuberculosis," Mucosal Immunol., Sep. 2013, pp. 972-984, vol. 6, No. 5.
Griffiths, K. et al., "Cholera Toxin Enhances Vaccine-Induced Protection against *Mycobacterium tuberculosis* Challenge in Mice," PLoS One, Oct. 2013, pp. 1-8, vol. 8, No. 10, e78312.
Griffiths, K. et al., "Novel vaccine approaches for protection against intracellular pathogens," Curr. Opin. Immunol., 2014, pp. 58-63, vol. 28.
Griffiths, K. et al., "Targeting dendritic cells to accelerate T-cell activation overcomes a bottleneck in tuberculosis vaccine efficacy," Nat. Commun., 2016, pp. 1-13, vol. 7, No. 13894.
Grode, L. et al., "Increased vaccine efficacy against tuberculosis of recombinant *Mycobacterium bovis* bacille Calmette-Guerin mutants that secret listeriolysin," J. Clin. Invest., 2005, pp. 2472-2479, vol. 115, No. 9.
Harding, C. et al., "Regulation of antigen presentation by *Mycobacterium tuberculosis*: a role for Toll-like receptors," NIH Public Access

(56) References Cited

OTHER PUBLICATIONS

Author Manuscript, Apr. 1, 2011, pp. 1-25, published in final edited form as: Nat. Rev. Microbiol., Apr. 2010, pp. 296-307, vol. 8, No. 4.
Hawkridge, T. et al., "Safety and Immunogenicity of a New Tuberculosis Vaccine, MVA85A, in Healthy Adults in South Africa," J. Infect. Dis., Aug. 2008, pp. 544-552, vol. 198.
Higgins, S. et al., "TLR4 Mediates Vaccine-Induced Protective Cellular Immunity to Bordetella pertussis: Role of IL-17-Producing T Cells," J. Immunol., 2006, pp. 7980-7989, vol. 177.
International Search Report and Written Opinion dated Jan. 22, 2019 from related Patent Application No. PCT/US2018/038296; 13 pgs.
Kaushal, D. et al., "Mucosal vaccination with attenuated *Mycobacterium tuberculosis* induces strong central memory responses and protects against tuberculosis," Nat. Commun., 2015, pp. 1-14, vol. 6, No. 8533.
Khader, S. et al., "IL-23 and IL-17 in the establishment of protective pulmonary CD4+ T cell responses after Vaccination and during *Mycobacterium tuberculosis* challenge," Nat. Immunol., Apr. 2007, pp. 369-377, vol. 8, No. 4.
Khader, S. et al., "In a Murine Tuberculosis Model, the Absence of Homeostatic Chemokines Delays Granuloma Formation and Protective Immunity," J. Immunol., 2009, pp. 8004-8014, vol. 183.
Khader, S. et al., "IL-23 is Required for Long-Term Control of *Mycobacterium tuberculosis* and B Cell Follicle Formation in the Infected Lung," J. Immunol., 2011, pp. 5402-5407, vol. 187.
Lee, J-B. et al., "Intranasal Delivery of Cholera Toxin Induces Th17-Dominated T-Cell Response to Bystander Antigens," PLoS One, Apr. 2009, pp. 1-9, vol. 4, No. 4, e5190.
Lienhardt, C. et al., "The blueprint for vaccine research & development: Walking the path for better TB vaccines," Tuberculosis, 2012, pp. S33-S35, vol. 91S1.
Malley, R. et al., "Antibody-Independent, Interleukin-17A-Mediated, Cross-Serotype Immunity to Pneumococci in Mice Immunized Intranasally with the Cell Wall Polysaccharide," Infect. Immun., Apr. 2006, pp. 2187-2195, vol. 74, No. 4.
Marcus, S. et al., "Protection by novel vaccine candidates, *Mycobacterium tuberculosis* DeltamosR and DeltaechA7, against challenge with a *Mycobacterium tuberculosis* Beijing strain," HHS Public Access Author Manuscript, Oct. 13, 2016, pp. 1-17, published in final edited form as: Vaccine, Oct. 2015, pp. 5633-5639, vol. 33, No. 42.
Martin, C. et al., "The live *Mycobacterium tuberculosis* phoP mutant strain is more attenuated than BCG and confers protective immunity against tuberculosis in mice and guinea pigs," Vaccine, 2006, pp. 3408-3419, vol. 24.
Mills, K. et al., "Protective Levels of Diphtheria-Neutralizing Antibody Induced in Healthy Volunteers by Unilateral Priming-Boosting Intranasal Immunization Associated with Restricted Ipsilateral Mucosal Secretory Immunoglobulin A," Infect. Immun., Feb. 2003, pp. 726-732, vol. 71, No. 2.

\* cited by examiner

BCG+NE:NE

BCG:NE

NANOEMULSION AND METHODS OF USE THEREOF

CROSS-REFERENCE TO RELATED APPLICATION

This application claims the benefit of U.S. Provisional Application No. 62/521,938, filed Jun. 19, 2017, and U.S. Provisional Application 62/530,548, filed Jul. 10, 2017, the disclosures of which are hereby incorporated by reference in their entirety.

GOVERNMENTAL RIGHTS

This invention was made with government support under grant number HL105427 awarded by National Institutes of Health. The government has certain rights in the invention.

FIELD OF THE INVENTION

The present disclosure relates to compositions and methods for inducing an immune response to a composition of the invention in a subject. Additionally, the present disclosure generally relates to methods for screening for immune response to a composition of the invention.

BACKGROUND

Tuberculosis (TB), caused by *Mycobacterium tuberculosis* (Mtb) is contracted via aerosol infection, typically affecting the lungs. TB causes 1.4 million deaths annually and is associated with substantial personal, social, public health, and economic costs, particularly in those individuals co-infected with HIV and other chronic diseases. Proper, accurate, and timely diagnosis of TB is essential to rapidly identify patients for treatment and targeted public health intervention to prevent spread of disease and minimize the emergence of drug resistant strains. Worldwide, most cases of TB are diagnosed using a sputum smear, clinical symptoms, and/or radiographs.

*Mycobacterium bovis* bacille Calmette-Guérin (BCG) is an attenuated strain derived from *Mycobacterium bovis*, and it is the only approved vaccine against TB to date. However, the effect of BCG on adults was found to be quite different, especially among different races. The effectiveness of BCG decreases with the increase of age, and thus it is not effective for preventing the disease in adults, especially in high TB areas. BCG vaccination has been used to prevent tuberculous meningitis and to facilitate the prevention of the spread of *Mycobacterium tuberculosis* to the lungs, but cannot prevent infection. Another limitation of the BCG vaccine is that parenteral delivery cannot induce potent T cell immunity in the lung mucosa, which is critical for the protection from *Mycobacterium tuberculosis*. Additionally, chemotherapy is associated with low compliance contributing to development of multidrug-resident (MDR) and extensively drug-resistant (XDR) Mtb.

What is needed, therefore, are safe and effective mucosal adjuvants for human use.

SUMMARY

One aspect of the present disclosure is directed to a composition. The composition of the invention comprises (a) an immune-enhancing nanoemulsion, or a dilution thereof and (b) at least isolated mycobacterial antigen, or an antigenic fragment thereof. The nanoemulsion comprises (i) an aqueous phase; (ii) about 1% to about 80% (v/v) of at least one oil; (iii) about 0.001% to about 10% (v/v) of at least one surfactant; (iv) about 0.01% to about 50% (v/v) of at least one solvent; and (v) less than about 5% (v/v) of at least one quaternary ammonium compound. The nanoemulsion consists of droplets with an average diameter of less than about 1,000 nm.

Another aspect of the present disclosure is directed to a method of inducing an immune response in a subject. The method comprises administering to the subject a composition of the invention comprising (a) a nanoemulsion and (b) at least one isolated mycobacterial antigen, or an antigenic fragment thereof. The nanoemulsion comprises (i) droplets having an average diameter of less than about 1,000 nm; (ii) an aqueous phase; (iii) about 1% to about 80% (v/v) of at least one oil; (iv) about 0.001% to about 10% (v/v) of at least one surfactant; (v) about 0.01% to about 50% (v/v) of at least one solvent; and (vi) less than about 5% (v/v) of at least one quaternary ammonium compound.

Yet another aspect of the present disclosure is directed to a method of screening a composition of the invention for an immune response. The method comprises (i) administering the composition to be screened to a screening platform; (ii) infecting the screening platform with a strain of mycobacteria; (iii) measuring the immune response in the screening platform; (iv) comparing the immune response of the screening platform in step (iii) to a control screen platform that was not administered the composition; wherein, if there is a difference, the composition elicits an immune response. In another aspect of the present disclosure, methods directed to screening a composition of the invention for an immune response may additionally include administering dendritic cells to the screening platform before, after or at the time of infecting the screening platform with a strain of mycobacteria.

Other aspects and iterations of the disclosure are described in more detail below.

BRIEF DESCRIPTION OF THE FIGURES

The application file contains at least one drawing executed in color. Copies of this patent application publication with color drawing(s) will be provided by the Office upon request and payment of the necessary fee.

FIG. 4A shows lung bacterial burden determined by plating. Flow cytometry was used to assess CD44 expression on $CD3^+$ $CD4^+$ T cells (FIG. 4B), IL-17 production (FIG. 4C), and IFN-γ production (FIG. 4D) by Ag85B-specific $CD4^+$ $CD44^{hi}$ T cells in harvested lungs. FIG. 4E shows flow cytometry was used to assess MHC-II mean fluorescence intensity (MFI) on lung alveolar macrophages. FIG. 4F shows representative plot of MHC-II expression on alveolar macrophages is shown at 8 dpi. *p 0.05, p 0.01, *p 0.001 by one way ANOVA or two way ANOVA. ND=not detected. Dotted lines on bacterial burden plots represent the limit of detection by plating.

DETAILED DESCRIPTION

Figure 1A:
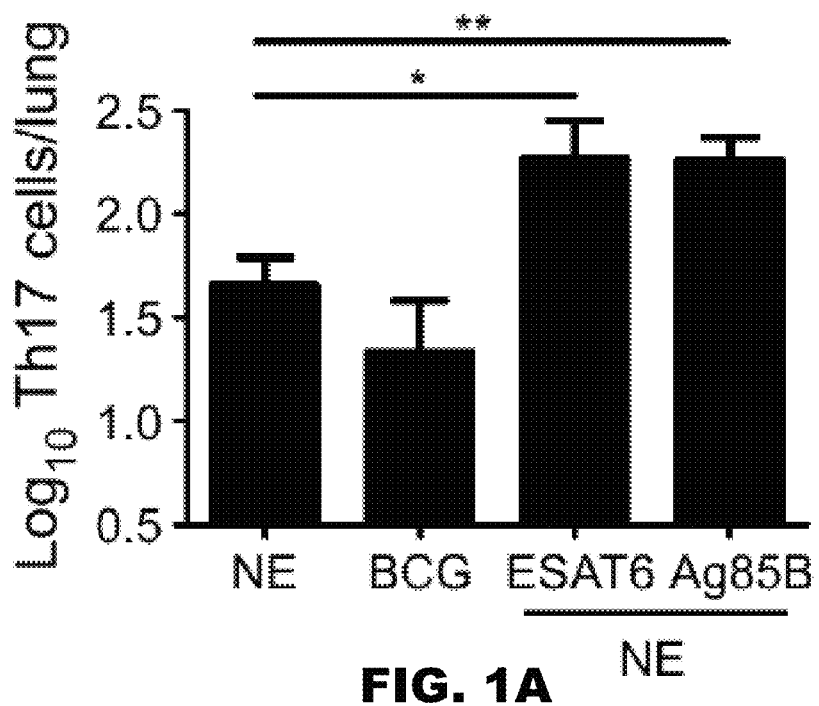
FIG. 1A, FIG. 1B, FIG. 1C, and FIG. 1D depict graphs showings NE-TB vaccine induces Th17 mucosal responses. Mice were mucosally vaccinated with Ag85B or ESAT-6 protein with nanoemulsion (NE) adjuvant by intranasal (i.n.) delivery or with BCG by subcutaneous (s.c.) injection 2 weeks later, Th1 response (FIG. 1C and FIG. 1D) or Th17 responses (FIG. 1A and FIG. 1B) were determined in lung and spleen by antigen-driven ELISpot assays. n=5.

Provided herein are compositions and methods for inducing an immune response in a subject as well as a method of screening a composition of the invention for an immune response. Suitable compositions and methods of the invention are discussed in more detail below.

(I) Nanoemulsion

In one aspect of the present disclosure the composition of the invention comprises a nanoemulsion. The nanoemulsion comprises an aqueous phase, an oil phase, at least one surfactant, at least one solvent, at least one antiseptic, and at least one antigen.

(a) Aqueous Phase

In general, the nanoemulsion comprises an aqueous phase. In some embodiments, the aqueous phase may comprise any type of aqueous phase including, without limit, distilled water, purified water, water for injection, de-ionized water, tap water and solutions (e.g., phosphate buffered saline (PBS) solution). The water may be deionized. In some embodiments, the aqueous phase may comprise phosphate buffered saline (PBS). The aqueous phase may further be sterile and pyrogen free.

In an embodiment, the pH of the aqueous phase may be from about 4 to about 10. In some embodiments, the pH of the aqueous phase may be about 4, about 4.5, about 5, about 5.5, about 6, about 6.5, about 7, about 7.5, about 8, about 8.5, about 9, about 9.5, or about 10. In a preferred embodiment, the pH of the aqueous phase may be from about 6 to about 8.

In some embodiments, the amount of the aqueous phase in the nanoemulsion can and will vary depending on the identity of the aqueous phase. In some embodiments, the amount of the aqueous phase in the nanoemulsion may be from about 35% (v/v) to about 75% (v/v). In other embodiments, the amount of the aqueous phase in the nanoemulsion may be about 35% (v/v), about 40% (v/v), about 45% (v/v), about 50% (v/v), about 55% (v/v), about 60% (v/v), about 65% (v/v), about 70% (v/v), or about 75% (v/v). In additional embodiments, the amount of the aqueous phase in the nanoemulsion may be about 50% (v/v), about 51% (v/v), about 52% (v/v), about 53% (v/v), about 54% (v/v), about 55% (v/v), about 56% (v/v), about 57% (v/v), about 58% (v/v), about 59% (v/v), or about 60% (v/v).

(b) Oil Phase

In general, the nanoemulsion comprises an oil phase. In an embodiment, the oil phase comprises at least one oil. In an embodiment, the at least one oil may be any cosmetically or pharmaceutically acceptable oil. The at least one oil can be volatile or non-volatile, and may be, without limit, animal oil, vegetable oil, natural oil, synthetic oil, hydrocarbon oils, silicone oils, semi-synthetic derivatives thereof, and combinations thereof.

Suitable oils include, without limit, mineral oil, squalene oil, flavor oils, silicon oil, essential oils, water insoluble vitamins, isopropyl stearate, butyl stearate, octyl palmitate, cetyl palmitate, tridecyl behenate, diisopropyl adipate, dioctyl sebacate, menthyl anthranhilate, cetyl octanoate, octyl salicylate, isopropyl myristate, neopentyl glycol dicarpate cetols, CERAPHYLS, decyl oleate, diisopropyl adipate, $C_{12}$-$C_{15}$ alkyl lactates, cetyl lactate, lauryl lactate, isostearyl neopentanoate, myristyl lactate, isocetyl stearoyl stearate, octyldodecyl stearoyl stearate, hydrocarbon oils, Isoparaffin, fluid paraffins, isododecane, petrolatum, argan oil, canola oil, chile oil, coconut oil, corn oil, cottonseed oil, flaxseed oil, grape seed oil, mustard oil, olive oil, palm oil, palm kernel oil, peanut oil, pine seed oil, poppy seed oil, pumpkin seed oil, rice bran oil, safflower oil, tea oil, truffle oil, vegetable oil, apricot (kernel) oil, jojoba oil (*Simmondsia chinensis* seed oil), grapeseed oil, macadamia oil, wheat germ oil, almond oil, rapeseed oil, gourd oil, soybean oil, sesame oil, hazelnut oil, maize oil, sunflower oil, hemp oil, bois oil, kuki nut oil, avocado oil, walnut oil, fish oil, berry oil, allspice oil, juniper oil, seed oil, almond seed oil, anise seed oil, celery seed oil, cumin seed oil, nutmeg seed oil, leaf oil, basil leaf oil, bay leaf oil, cinnamon leaf oil, common sage leaf oil, eucalyptus leaf oil, lemon grass leaf oil, melaleuca leaf oil, oregano leaf oil, patchouli leaf oil, peppermint leaf oil, pine needle oil, rosemary leaf oil, spearmint leaf oil, tea tree leaf oil, thyme leaf oil, wintergreen leaf oil, flower oil, chamomile oil, clary sage oil, clove oil, geranium flower oil, hyssop flower oil, jasmine flower oil, lavender flower oil, manuka flower oil, marhoram flower oil, orange flower oil, rose flower oil, ylang-ylang flower oil, bark oil, cassia bark oil, cinnamon bark oil, sassafras bark oil, wood oil, camphor wood oil, cedar wood oil, rosewood oil, sandalwood oil), rhizome (ginger) wood oil, resin oil, frankincense oil, myrrh oil, peel oil, bergamot peel oil, grapefruit peel oil, lemon peel oil, lime peel oil, orange peel oil, tangerine peel oil, root oil, valerian oil, oleic acid, linoleic acid, oleyl alcohol, isostearyl alcohol, semi-synthetic derivatives thereof, and any combinations thereof.

In an embodiment, the at least one oil may further comprise a silicone component, such as a volatile silicone component, which can be the sole oil in the silicone component or can be combined with other silicone and non-silicone, volatile and non-volatile oils. Suitable silicone components include, without limit, methylphenylpolysiloxane, simethicone, dimethicone, phenyltrimethicone (or an organomodified version thereof), alkylated derivatives of polymeric silicones, cetyl dimethicone, lauryl trimethicone, hydroxylated derivatives of polymeric silicones, such as dimethiconol, volatile silicone oils, cyclic and linear silicones, cyclomethicone, derivatives of cyclomethicone, hexamethylcyclotrisiloxane, octamethylcyclotetrasiloxane, decamethylcyclopentasiloxane, volatile linear dimethylpolysiloxanes, isohexadecane, isoeicosane, isotetracosane, polyisobutene, isooctane, isododecane, semi-synthetic derivatives thereof, and combinations thereof.

In some embodiments, the volatile oil may be the organic solvent, or the volatile oil can be present in addition to an organic solvent. Suitable volatile oils include, without limit, a terpene, monoterpene, sesquiterpene, carminative, azulene, menthol, camphor, thujone, thymol, nerol, linalool, limonene, geraniol, perillyl alcohol, nerolidol, farnesol, ylangene, bisabolol, farnesene, ascaridole, chenopodium oil, citronellal, citral, citronellol, chamazulene, yarrow, guaiazulene, chamomile, semi-synthetic derivatives, or combinations thereof.

In some embodiments, the amount of at least one oil in the nanoemulsion can and will vary depending on the identity of the oil. In some embodiments, the amount of oil in the nanoemulsion may be from about 1% (v/v) to about 80% (v/v). In other embodiments, the amount of oil in the nanoemulsion may be about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 15% (v/v), about 20% (v/v), about 25% (v/v), about 30% (v/v), about 35% (v/v), about 40% (v/v), about 45% (v/v), about 50% (v/v), about 55% (v/v), about 60% (v/v), about 65% (v/v), about 70% (v/v), about 75% (v/v), or about 80% (v/v).

(c) Surfactant

In general, the nanoemulsion comprises at least one surfactant. In some embodiments, the surfactant may be a pharmaceutically acceptable ionic surfactant, a pharmaceutically acceptable nonionic surfactant, a pharmaceutically acceptable cationic surfactant, a pharmaceutically acceptable anionic surfactant, or a pharmaceutically acceptable zwitterionic surfactant.

In some embodiments, the surfactant may be a pharmaceutically acceptable ionic polymeric surfactant, a pharmaceutically acceptable nonionic polymeric surfactant, a pharmaceutically acceptable cationic polymeric surfactant, a pharmaceutically acceptable anionic polymeric surfactant, or a pharmaceutically acceptable zwitterionic polymeric surfactant. Polymeric surfactants include, without limit, a graft copolymer of a poly(methyl methacrylate) backbone with multiple (at least one) polyethylene oxide (PEO) side chain, polyhydroxystearic acid, an alkoxylated alkyl phenol formaldehyde condensate, a polyalkylene glycol modified polyester with fatty acid hydrophobes, a polyester, semi-synthetic derivatives thereof, or combinations thereof.

Suitable surfactants include, without limit, ethoxylated nonylphenol comprising 9 to 10 units of ethyleneglycol, ethoxylated undecanol comprising 8 units of ethyleneglycol, polyoxyethylene (20) sorbitan monolaurate, polyoxyethylene (20) sorbitan monopalmitate, polyoxyethylene (20) sorbitan monostearate, polyoxyethylene (20) sorbitan monooleate (i.e., polysorbate 80), sorbitan monolaurate, sorbitan monopalmitate, sorbitan monostearate, sorbitan monooleate, ethoxylated hydrogenated ricin oils, sodium laurylsulfate, a diblock copolymer of ethyleneoxide and propyleneoxide, ethylene oxide-propylene oxide block copolymers, and tetra-functional block copolymers based on ethylene oxide and propylene oxide, Glyceryl monoesters, glyceryl caprate, glyceryl caprylate, glyceryl cocate, glyceryl erucate, glyceryl hydroxysterate, glyceryl isostearate, glyceryl lanolate, glyceryl laurate, glyceryl linolate, glyceryl myristate, glyceryl oleate, glyceryl PABA, glyceryl palmitate, glyceryl ricinoleate, glyceryl stearate, glyceryl thiglycolate, glyceryl dilaurate, glyceryl dioleate, glyceryl dimyristate, glyceryl disterate, glyceryl sesuioleate, glyceryl stearate lactate, polyoxyethylene cetyl/stearyl ether, polyoxyethylene cholesterol ether, polyoxyethylene laurate or dilaurate, polyoxyethylene stearate or distearate, polyoxyethylene fatty ethers, polyoxyethylene lauryl ether, polyoxyethylene stearyl ether, polyoxyethylene myristyl ether, a steroid, cholesterol, betasitosterol, Bisabolol, fatty acid esters of alcohols, isopropyl myristate, aliphati-isopropyl n-butyrate, Isopropyl n-hexanoate, Isopropyl n-decanoate, Isoproppyl palm itate, octyldodecyl myristate, alkoxylated alcohols, alkoxylated acids, alkoxylated amides, alkoxylated sugar derivatives, alkoxylated derivatives of natural oils and waxes, polyoxyethylene polyoxypropylene block copolymers, nonoxynol-14, PEG-8 laurate, PEG-6 Cocoamide, PEG-20 methylglucose sesquistearate, PEG-40 lanolin, PEG-40 castor oil, PEG-40 hydrogenated castor oil, polyoxyethylene fatty ethers, glyceryl diesters, polyoxyethylene stearyl ether, polyoxyethylene myristyl ether, and polyoxyethylene lauryl ether, glyceryl dilaurate, glyceryl dimystate, glyceryl distearate, semi-synthetic derivatives thereof, or mixtures thereof.

Additional suitable surfactants include, without limit, non-ionic lipids, such as glyceryl laurate, glyceryl myristate, glyceryl dilaurate, glyceryl dimyristate, semi-synthetic derivatives thereof, and mixtures thereof.

In additional embodiments, the at least one surfactant may be a polyoxyethylene fatty ether having a polyoxyethylene head group ranging from about 2 to about 100 groups, or an alkoxylated alcohol having the structure $R^5$—$(OCH_2 CH_2)$ y-OH, wherein $R^5$ is a branched or unbranched alkyl group having from about 6 to about 22 carbon atoms and y is between about 4 and about 100, and preferably, between about 10 and about 100. In a preferred embodiment, the alkoxylated alcohol is the species wherein $R^5$ is a lauryl group and y has an average value of 23.

In a different embodiment, the at least one surfactant may be an alkoxylated alcohol which is an ethoxylated derivative of lanolin alcohol. Preferably, the ethoxylated derivative of lanolin alcohol is laneth-10, which is the polyethylene glycol ether of lanolin alcohol with an average ethoxylation value of 10.

Nonionic surfactants include, without limit, an ethoxylated surfactant, an alcohol ethoxylated, an alkyl phenol ethoxylated, a fatty acid ethoxylated, a monoalkaolamide ethoxylated, a sorbitan ester ethoxylated, a fatty amino ethoxylated, an ethylene oxide-propylene oxide copolymer, bis(polyethylene glycol bis[imidazoyl carbonyl]), nonoxynol-9, Bis(polyethylene glycol bis[imidazoyl carbonyl]), BRIJ 35, BRIJ 56, BRIJ 72, BRIJ 76, BRIJ 92V, BRIJ 97, BRIJ 58P, CREMOPHOR EL, decaethylene glycol monododecyl ether, N-decanoyl-N-methylglucamine, n-decyl alpha-D-glucopyranoside, decyl beta-D-maltopyranoside, n-dodecanoyl-N-methylglucamide, n-dodecyl alpha-D-maltoside, n-Dodecyl beta-D-maltoside, n-dodecyl beta-D-maltoside, heptaethylene glycol monodecyl ether, heptaethylene glycol monododecyl ether, heptaethylene glycol monotetradecyl ether, n-hexadecyl beta-D-maltoside, hexaethylene glycol monododecyl ether, hexaethylene glycol monohexadecyl ether, hexaethylene glycol monooctadecyl ether, hexaethylene glycol monotetradecyl ether, igepal CA-630, igepal CA-630, methyl-6-O—(N-heptylcarbamoyl)-alpha-D-glucopyranoside, nonaethylene glycol monododecyl ether, N-nonanoyl-N-methylglucam ine, N-nonanoyl-N-methylglucamine, octaethylene glycol monodecyl ether, octaethylene glycol monododecyl ether, octaethylene glycol monohexadecyl ether, octaethylene glycol monooctadecyl ether, octaethylene glycol monotetradecyl ether, octyl-beta-D-glucopyranoside, pentaethylene glycol monodecyl ether, pentaethylene glycol monododecyl ether, pentaethylene glycol monohexadecyl ether, pentaethylene glycol monohexyl ether, pentaethylene glycol monooctadecyl ether, pentaethylene glycol monooctyl ether, polyethylene glycol diglycidyl ether, polyethylene glycol ether W-1, polyoxyethylene 10 tridecyl ether, polyoxyethylene 100 stearate, polyoxyethylene 20 isohexadecyl ether, polyoxyethylene 20 oleyl ether, polyoxyethylene 40 stearate, polyoxyethylene 50 stearate, polyoxyethylene 8 stearate, polyoxyethylene bis(imidazolyl carbonyl), polyoxyethylene 25 propylene glycol stearate, saponin from quillaja bark, SPAN 20, SPAN 40, SPAN 60, SPAN 65, SPAN 80, SPAN 85, Tergitol, Type 15-S-12, tergitol, Type 15-S-30, tergitol, Type 15-S-5, tergitol, Type 15-S-7, tergitol, Type 15-S-9, tergitol, Type NP-10, tergitol, Type NP-4, tergitol, Type NP-40, tergitol, Type NP-7, tergitol, Type NP-9, tergitol, Tergitol, Type TMN-10, tergitol, Type TMN-6, tetradecyl-beta-D-maltoside, tetraethylene glycol monodecyl ether, tetraethylene glycol monododecyl ether, tetraethylene glycol monotetradecyl ether, triethylene glycol monodecyl ether, triethylene glycol monododecyl ether, triethylene glycol monohexadecyl ether, triethylene glycol monooctyl ether, triethylene glycol monotetradecyl ether, TRITON CF-21, TRITON CF-32, TRITON DF-12, TRITON DF-16, TRITON GR-5M, TRITON QS-15, TRITON QS-44, TRITON X-100, TRITON X-102, TRITON X-15, TRITON X-151, TRITON X-200, TRITON X-207, TRITON X-100, TRITON X-114, TRITON X-165, TRITON X-305, TRITON X-405, TRITON X-45, TRITON X-705-70, TWEEN 20, TWEEN 21, TWEEN 40, TWEEN 60, TWEEN 61, TWEEN 65, TWEEN 80, TWEEN 81, TWEEN 85, tyloxapol, n-undecyl beta-D-glucopyranoside, semi-synthetic derivatives thereof, or combinations thereof.

In addition, the nonionic surfactant may be a poloxamer. Poloxamers are polymers made of a block of polyoxyethylene, followed by a block of polyoxypropylene, followed by a block of polyoxyethylene. The average number of units of polyoxyethylene and polyoxypropylene varies based on the number associated with the polymer. For example, the smallest polymer, poloxamer 101, consists of a block with an average of 2 units of polyoxyethylene, a block with an average of 16 units of polyoxypropylene, followed by a block with an average of 2 units of polyoxyethylene. Poloxamers range from colorless liquids and pastes to white solids. In cosmetics and personal care products, poloxamers are used in the formulation of skin cleansers, bath products, shampoos, hair conditioners, mouthwashes, eye makeup remover and other skin and hair products. Examples of poloxamers include, without limit, poloxamer 101, poloxamer 105, poloxamer 108, poloxamer 122, poloxamer 123, poloxamer 124, poloxamer 181, poloxamer 182, poloxamer 183, poloxamer 184, poloxamer 185, poloxamer 188, poloxamer 212, poloxamer 215, poloxamer 217, poloxamer 231, poloxamer 234, poloxamer 235, poloxamer 237, poloxamer 238, poloxamer 282, poloxamer 284, poloxamer 288, poloxamer 331, poloxamer 333, Poloxamer 334, poloxamer 335, poloxamer 338, poloxamer 401, poloxamer 402, poloxamer 403, poloxamer 407, poloxamer 105 benzoate, and poloxamer 182 dibenzoate.

Suitable anionic surfactants include, without limit, a carboxylate, a sulphate, a sulphonate, a phosphate, chenodeoxycholic acid, chenodeoxycholic acid sodium salt, cholic acid, ox or sheep bile, dehydrocholic acid, deoxycholic acid, deoxycholic acid, deoxycholic acid methyl ester, digitonin, digitoxigenin, N,N-dimethyldodecyl amine N-oxide, docusate sodium salt, glycochenodeoxycholic acid sodium salt, glycocholic acid hydrate, synthetic, glycocholic acid sodium salt hydrate, synthetic, glycodeoxycholic acid monohydrate, glycodeoxycholic acid sodium salt, glycodeoxycholic acid sodium salt, glycolithocholic acid 3-sulfate disodium salt, glycolithocholic acid ethyl ester, N-lauroylsarcosine sodium salt, N-lauroylsarcosine solution, N-lauroylsarcosine solution, lithium dodecyl sulfate, lithium dodecyl sulfate, Lithium dodecyl sulfate, Lugol solution, Niaproof 4, Type 4, 1-Octanesulfonic acid sodium salt, sodium 1-butanesulfonate, sodium 1-decanesulfonate, sodium 1-decanesulfonate, sodium 1-dodecanesulfonate, sodium 1-heptanesulfonate anhydrous, sodium 1-heptanesulfonate anhydrous, sodium 1-nonanesulfonate, sodium 1-propanesulfonate monohydrate, sodium 2-bromoethanesulfonate, sodium cholate hydrate, sodium choleate, sodium deoxycholate, sodium deoxycholate monohydrate, sodium dodecyl sulfate, sodium hexanesulfonate anhydrous, sodium octyl sulfate, sodium pentanesulfonate anhydrous, sodium taurocholate, taurochenodeoxycholic acid sodium salt, taurodeoxycholic acid sodium salt monohydrate, taurohyodeoxycholic acid sodium salt hydrate, taurolithocholic acid 3-sulfate disodium salt, tauroursodeoxycholic acid sodium salt, TRIZMA dodecyl sulfate, TWEEN 80, ursodeoxycholic acid, semi-synthetic derivatives thereof, and combinations thereof.

Suitable zwitterionic surfactants include, without limit, an N-alkyl betaine, lauryl amido propyl dimethyl betaine, an alkyl dimethyl glycinate, an N-alkyl amino propionate, CHAPS, minimum 98% (TLC), CHAPS, SigmaUltra, minimum 98% (TLC), CHAPS, for electrophoresis, minimum 98% (TLC), CHAPSO, minimum 98%, CHAPSO, SigmaUltra, CHAPSO, for electrophoresis, 3-(decyldimethylammonio) propanesulfonate inner salt, 3-dodecyldimethylammonio) propanesulfonate inner salt, SigmaUltra, 3-(dodecyldimethylammonio) propanesulfonate inner salt, 3-(N,N-dimethylmyristylammonio) propanesulfonate, 3-(N,N-dimethyloctadecylammonio) propanesulfonate, 3-(N,N-dimethyloctylammonio) propanesulfonate inner salt, 3-(N,N-dimethylpalmitylammonio)propanesulfonate, semi-synthetic derivatives thereof, and combinations thereof.

In an exemplary embodiment, the at least one surfactant in the nanoemulsion may comprise polysorbate 20, polysorbate 80, and combinations thereof. In another exemplary embodiment, the at least one surfactant in the nanoemulsion may comprise polysorbate 20 and polysorbate 80.

In an embodiment, the amount of the at least one surfactant in the nanoemulsion may be from about 0.001% (v/v) to about 10% (v/v). In some embodiments, the amount of the at least one surfactant in the nanoemulsion may be about 0.001% (v/v), about 0.005% (v/v), about 0.01% (v/v), about 0.015% (v/v), about 0.02% (v/v), about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), about 0.1% (v/v), about 0.15% (v/v), about 0.2% (v/v), about 0.25% (v/v), about 0.3% (v/v), about 0.35% (v/v), about 0.4% (v/v), about 0.45% (v/v), about 0.5% (v/v), about 1.0% (v/v), about 1.5%, (v/v), about 2.0% (v/v), about 2.5% (v/v), about 3.0% (v/v), about 3.5% (v/v), about 4.0% (v/v), about 4.5% (v/v), about 5.0% (v/v), about 5.5% (v/v), about 6.0% (v/v), about 6.5% (v/v), about 7.0% (v/v), about 7.5% (v/v), about 8% (v/v), about 8.5% (v/v), about 9% (v/v), about 9.5% (v/v), or about 10% (v/v).

(d) Solvent

In general, the nanoemulsion comprises at least one solvent. In some embodiments, the at least one solvent may include, without limit, $C_1$-$C_{12}$ alcohol, diol, triol, dialkyl phosphate, tri-alkyl phosphate, such as tri-n-butyl phosphate, semi-synthetic derivatives thereof, and combinations thereof. In one aspect of the invention, the solvent is an alcohol chosen from a nonpolar solvent, a polar solvent, a protic solvent, or an aprotic solvent.

Suitable solvents include, without limit, ethanol, methanol, isopropyl alcohol, glycerol, medium chain triglycerides, diethyl ether, ethyl acetate, acetone, dimethyl sulfoxide (DMSO), acetic acid, n-butanol, butylene glycol, perfumers alcohols, isopropanol, n-propanol, formic acid, propylene glycols, glycerol, sorbitol, industrial methylated spirit, triacetin, hexane, benzene, toluene, diethyl ether, chloroform, 1,4-dixoane, tetrahydrofuran, dichloromethane, acetone, acetonitrile, dimethylformamide, dimethyl sulfoxide, formic acid, semi-synthetic derivatives thereof, and any combination thereof.

In an embodiment, the amount of the at least one solvent in the nanoemulsion may be from about 0.01% (v/v) to about 50% (v/v). In some embodiments, the amount of the at least one solvent in the nanoemulsion may be about 0.01% (v/v), about 0.05% (v/v), about 0.1% (v/v), about 0.15% (v/v), about 0.2% (v/v), about 0.25% (v/v), about 0.3% (v/v), about 0.35% (v/v), about 0.4% (v/v), about 0.45% (v/v), about 0.5% (v/v), about 1.0% (v/v), about 1.5%, (v/v), about 2.0% (v/v), about 2.5% (v/v), about 3.0% (v/v), about 3.5% (v/v), about 4.0% (v/v), about 4.5% (v/v), about 5.0% (v/v), about 10% (v/v), about 15% (v/v), about 20% (v/v), about 25% (v/v), about 30% (v/v), about 35% (v/v), about 40% (v/v), about 45% (v/v), or about 50% (v/v).

(e) Antiseptic

In general, the nanoemulsion comprises at least one antiseptic. In some embodiments, the at least one antiseptic may be a cationic surfactant, a quaternary ammonium compound, an alkyl trimethyl ammonium chloride compound, a dialkyl dimethyl ammonium chloride compound, a cationic halogen-containing compound.

Suitable antiseptic agents include, without limit, cetylpyridinium chloride (CPC), benzalkonium chloride, benzalkonium chloride, benzyldimethylhexadecylammonium chloride, benzyldimethyltetradecylammonium chloride, benzyldodecyldimethylammonium bromide, benzyltrimethylammonium tetrachloroiodate, dimethyldioctadecylammonium bromide, dodecylethyldimethylammonium bromide, dodecyltrimethylammonium bromide, dodecyltrimethylammonium bromide, ethylhexadecyldimethylammonium bromide, Girard's reagent T, hexadecyltrimethylammonium bromide, hexadecyltrimethylammonium bromide, N,N',N'-polyoxyethylene(10)-N-tallow-1,3-diaminopropane, thonzonium bromide, trimethyl(tetradecyl)ammonium bromide, 1,3,5-triazine-1,3,5(2H, 4H,6H)-triethanol, 1-decanaminium, N-decyl-N,N-dimethyl-, chloride, didecyl dimethyl ammonium chloride, 2-(2-(p-Diisobutyl)cresosxy)ethoxy)ethyl dimethyl benzyl ammonium chloride, 2-(2-(p-(Diisobutyl)phenoxy)ethoxy) ethyl dimethyl benzyl ammonium chloride, alkyl 1 or 3 benzyl-1-(2-hydroxethyl)-2-imidazolinium chloride, alkyl bis(2-hydroxyethyl)benzyl ammonium chloride, alkyl demethyl benzyl ammonium chloride, alkyl dimethyl 3,4-dichlorobenzyl ammonium chloride (100% $C_{12}$), alkyl dimethyl 3,4-dichlorobenzyl ammonium chloride (50% $C_{14}$, 40% $C_{12}$, 10% $C_{16}$), alkyl dimethyl 3,4-dichlorobenzyl ammonium chloride (55% $C_{14}$, 23% $C_{12}$, 20% $C_{16}$), alkyl dimethyl benzyl ammonium chloride, alkyl dimethyl benzyl ammonium chloride (100% $C_{14}$), alkyl dimethyl benzyl ammonium chloride (100% $C_{16}$), alkyl dimethyl benzyl ammonium chloride (41% $C_{14}$, 28% $C_{12}$), alkyl dimethyl benzyl ammonium chloride (47% $C_{12}$, 18% $C_{14}$), alkyl dimethyl benzyl ammonium chloride (55% $C_{16}$, 20% $C_{14}$), alkyl dimethyl benzyl ammonium chloride (58% $C_{14}$, 28% $C_{16}$), alkyl dimethyl benzyl ammonium chloride (60% $C_{14}$, 25% $C_{12}$), alkyl dimethyl benzyl ammonium chloride (61% $C_{11}$, 23% $C14$), alkyl dimethyl benzyl ammonium chloride (61% $C_{12}$, 23% $C_{14}$), alkyl dimethyl benzyl ammonium chloride (65% $C_{12}$, 25% $C_{14}$), alkyl dimethyl benzyl ammonium chloride (67% $C_{12}$, 24% $C_{14}$), alkyl dimethyl benzyl ammonium chloride (67% $C_{12}$, 25% $C_{14}$), alkyl dimethyl benzyl ammonium chloride (90% $C_{14}$, 5% $C_{12}$), alkyl dimethyl benzyl ammonium chloride (93% $C_{14}$, 4% $C_{12}$), alkyl dimethyl benzyl ammonium chloride (95% $C_{16}$, 5% $C_{18}$), alkyl dimethyl benzyl ammonium chloride, alkyl didecyl dimethyl ammonium chloride, alkyl dimethyl benzyl ammonium chloride, alkyl dimethyl benzyl ammonium chloride ($C_{12}$-$C_{16}$), alkyl dimethyl benzyl ammonium chloride ($C_{12}$-$C_{18}$), alkyl dimethyl benzyl ammonium chloride, dialkyl dimethyl benzyl ammonium chloride, alkyl dimethyl dimethybenzyl ammonium chloride, alkyl dimethyl ethyl ammonium bromide (90% $C_{14}$, 5% $C_{16}$, 5% $C_{12}$), alkyl dimethyl ethyl ammonium bromide (mixed alkyl and alkenyl groups as in the fatty acids of soybean oil), alkyl dimethyl ethylbenzyl ammonium chloride, alkyl dimethyl ethylbenzyl ammonium chloride (60% $C_{14}$), alkyl dimethyl isopropylbenzyl ammonium chloride (50% $C_{12}$, 30% $C_{14}$, 17% $C_{16}$, 3% $C_{18}$), alkyl trimethyl ammonium chloride (58% $C_{18}$, 40% $C_{16}$, 1% $C_{14}$, 1% $C_{12}$), Alkyl trimethyl ammonium chloride (90% $C_{18}$, 10% $C_{16}$), alkyldimethyl(ethylbenzyl) ammonium chloride ($C_{12}$-$C_{18}$), dimethyl ammonium chlorides, dialkyl dimethyl ammonium chloride, dialkyl methyl benzyl ammonium chloride, didecyl dimethyl ammonium chloride, diisodecyl dimethyl ammonium chloride, dioctyl dimethyl ammonium chloride, dodecyl bis(2-hydroxyethyl)octyl hydrogen ammonium chloride, dodecyl dimethyl benzyl ammonium chloride, dodecylcarbamoyl methyl dinethyl benzyl ammonium chloride, heptadecyl hydroxyethylimidazolinium chloride, hexahydro-1,3,5-tris(2-hydroxyethyl)-s-triazine, Hexahydro-1,3,5-tris(2-hydroxyethyl)-s-triazine, myristalkonium chloride (and) Quat RNIUM 14, N,N-Dimethyl-2-hydroxypropylammonium chloride polymer, n-Tetradecyl dimethyl benzyl ammonium chloride monohydrate, octyl decyl dimethyl ammonium chloride, octyl dodecyl dimethyl ammonium chloride, octyphenoxyethoxyethyl dimethyl benzyl ammonium chloride, oxydiethylenebis(alkyl dimethyl ammonium chloride), quaternary ammonium compounds, dicoco alkyldimethyl, chloride, trimethoxysily propyl dimethyl octadecyl ammonium chloride, trimethoxysilyl quats, trimethyl dodecylbenzyl ammonium chloride, semi-synthetic derivatives thereof, and combinations thereof.

Suitable cationic halogen-containing compounds include, without limit, cetylpyridinium halides, cetyltrimethylammonium halides, cetyldimethylethylammonium halides, cetyldimethylbenzylammonium halides, cetyltributylphosphonium halides, dodecyltrimethylammonium halides, or tetradecyltrimethylammonium halides. Suitable cationic halogen containing compounds comprise, without limit, cetylpyridinium chloride (CPC), cetyltrimethylammonium chloride, cetylbenzyldimethylammonium chloride, cetylpyridinium bromide (CPB), cetyltrimethylammonium bromide (CTAB), cetyidimethylethylammonium bromide, cetyltributylphosphonium bromide, dodecyltrimethylammonium bromide, and tetrad ecyltrimethylammonium bromide. In a preferred embodiment, the at least one antiseptic may be cetylpyridinium chloride (CPC).

In an embodiment, the amount of the at least one antiseptic in the nanoemulsion may be from about 0.001% (v/v) to about 5.0% (v/v). In some embodiments, the amount of the at least one antiseptic in the nanoemulsion may be about 0.001% (v/v), about 0.005% (v/v), about 0.01% (v/v), about 0.015% (v/v), about 0.02% (v/v), about 0.025% (v/v), about 0.03% (v/v), about 0.035% (v/v), about 0.04% (v/v), about 0.045% (v/v), about 0.05% (v/v), about 0.055% (v/v), about 0.06% (v/v), about 0.065% (v/v), about 0.07% (v/v), about 0.075% (v/v), about 0.08% (v/v), about 0.085% (v/v), about 0.09% (v/v), about 0.095% (v/v), about 0.1% (v/v), about 0.15% (v/v), about 0.2% (v/v), about 0.25% (v/v), about 0.3% (v/v), about 0.35% (v/v), about 0.4% (v/v), about 0.45% (v/v), about 0.5% (v/v), about 1.0% (v/v), about 1.5%, (v/v), about 2.0% (v/v), about 2.5% (v/v), about 3.0% (v/v), about 3.5% (v/v), about 4.0% (v/v), about 4.5% (v/v), or about 5.0% (v/v). In some embodiments, the amount of the at least one antiseptic in the nanoemulsion may be less than about 5% (v/v).

(f) Antigen

In general, the nanoemulsion comprises at least one antigen. As used herein, "antigen" refers to an amino acid sequence that elicits an immune response. In some embodiments, the at least one antigen may comprise at least one isolated mycobacterial antigen, or an antigenic fragment thereof. In some embodiments, the at least one antigen may comprise at least one isolated *Mycobacterium* species antigen, or an antigenic fragment thereof. Non-limiting examples of *Mycobacterium* species may include *Mycobacterium avium* complex (MAC), *Mycobacterium kansasii*, *Mycobacterium xenopi*, *Mycobacterium marinum*, *Mycobacterium ulcerans*, the *Mycobacterium fortuitum* complex (*Mycobacterium fortuitum*, *Mycobacterium abscessus*, and *Mycobacterium chelonae*), *Mycobacterium gordonae*, *Mycobacterium abscessus*, and *Mycobacterium tuberculosis* complex ((MTBC) *Mycobacterium africanum*, *Mycobacterium bovis*, *Mycobacterium canetti*, *Mycobacterium caprae*, *Mycobacterium microti*, *Mycobacterium mungi*, *Mycobacterium orygis*, *Mycobacterium pinnipedii*, *Mycobacterium suricattae*, *Mycobacterium tuberculosis*). In a preferred embodiment, the at least one antigen may comprise at least one isolated *Mycobacterium tuberculosis* antigen, or an antigenic fragment thereof. If the antigen comprises a fragment, then the fragment is sufficient to induce an immune response. If the antigen comprises a mutated protein, then the mutated protein is sufficient to induce an immune response. In some embodiments, the at least one antigen may comprise at least one mutated protein secreted from mycobacteria. In some embodiments, the at least one antigen may comprise at least one mutated protein secreted from a species of *Mycobacterium*. Non-limiting examples of *Mycobacterium* species may include *Mycobacterium avium* complex (MAC), *Mycobacterium kansasii*, *Mycobacterium xenopi*, *Mycobacterium marinum*, *Mycobacterium ulcerans*, the *Mycobacterium fortuitum* complex (*Mycobacterium for-* *tuitum*, *Mycobacterium abscessus*, and *Mycobacterium chelonae*), *Mycobacterium gordonae*, *Mycobacterium abscessus*, and *Mycobacterium tuberculosis* complex ((MTBC) *Mycobacterium africanum*, *Mycobacterium bovis*, *Mycobacterium canetti*, *Mycobacterium caprae*, *Mycobacterium microti*, *Mycobacterium mungi*, *Mycobacterium orygis*, *Mycobacterium pinnipedii*, *Mycobacterium suricattae*, *Mycobacterium tuberculosis*). In a preferred embodiment, the at least one antigen may comprise at least one mutated protein secreted from *Mycobacterium tuberculosis*. In some embodiments, the at least one isolated *Mycobacterium tuberculosis* antigen, or an antigenic fragment thereof may comprise, without limit, ESAT-6 (accession reference number: AHN50413), CFP10 (accession reference number: AHN50412), Hsp16.3 (accession reference number: CCP44804), MTB32A (accession reference number: CCP42850), MTB39A (accession reference number: CCP43952), Ag85A (accession reference number: P9WQP3), Ag85B (accession reference number: A5U3Q3), Ag85C (accession reference number: P9WQN8), Rv1733c (accession reference number: CCP44499), Rv2626c (accession reference number: CCP45424), Rv3407 (accession reference number: CCP46229), Rv2628 (accession reference number: CCP45426), RpfB (accession reference number: CCE36540), RpfD (accession reference number: CCE37859), RpfE (accession reference number: CCE37920), and combinations thereof. In a preferred embodiment, the at least one antigen may be ESAT-6, CFP10, Hsp16.3, MTB32A, MTB39A, Ag85A, Ag85B, Ag85C, Rv1733c, Rv2626, RpfD, and combinations thereof. In an embodiment, the at least one isolated *Mycobacterium tuberculosis* antigen, or an antigenic fragment thereof may comprise ESAT-6 and Ag85B. In a non-limiting examples, secreted protein from *Mycobacterium tuberculosis* are described in Zhang, C., et al. Journal of Clinical Lab Anal, (2015), 29(5): 375-382, herein incorporated by reference in its entirety.

In an embodiment, the amount of the at least one isolated mycobacterial antigen, or an antigenic fragment thereof in the nanoemulsion may be from about 10 µg to about 50 µg. In some embodiments, the amount of the at least one isolated mycobacterial antigen, or an antigenic fragment thereof in the nanoemulsion may be about 10 µg, about 15 µg, about 20 µg, about 25 µg, about 30 µg, about 35 µg, about 40 µg, about 45 µg, or about 50 µg. In a preferred embodiment, the amount of the at least one isolated mycobacterial antigen, or an antigenic fragment thereof may be about 25 µg.

(g) Droplet Size

In general, the nanoemulsion is formulated into droplets. In an embodiment, the nanoemulsion consists of droplets having an average diameter of from about 50 nm to about 1,000 nm. In some embodiments, the nanoemulsion comprises droplets having an average diameter of about 50 nm, about 60 nm, about 70 nm, about 80 nm, about 90 nm, about 100 nm, about 125 nm, about 150 nm, about 175 nm, about 200 nm, about 225 nm, about 250 nm, about 275 nm, about 300 nm, about 325 nm, about 350 nm, about 375 nm, about 400 nm, about 425 nm, about 450 nm, about 475 nm, about 500 nm, about 525 nm, about 550 nm, about 575 nm, about 600 nm, about 625 nm, about 650 nm, about 675 nm, about 700 nm, about 725 nm, about 750 nm, about 775 nm, about 800 nm, about 825 nm, about 850 nm, about 875 nm, about 900 nm, about 925 nm, about 950 nm, about 975 nm, or about 1,000 nm. In some embodiments, the nanoemulsion comprises droplets having an average diameter of less than 700 nm or less than 400 nm. In a preferred embodiment, the nanoemulsion comprises droplets having an average diameter of less than 7400 nm.

(h) Buffer

In an embodiment, the composition of the invention comprising a nanoemulsion may comprise a buffering agent, such as a pharmaceutically acceptable buffering agent. Buffering agents include, without limit, 2-amino-2-methyl-1,3-propanediol, ≥99.5% (NT), 2-amino-2-methyl-1-propanol, ≥99.0% (GC), L-(+)-tartaric acid, ≥99.5% (T), ACES, ≥99.5% (T), ADA, ≥99.0% (T), acetic acid, ≥99.5% (GC/T), acetic acid, for luminescence, ≥99.5% (GC/T), ammonium acetate solution, for molecular biology, ~5 M in $H_2O$, ammonium acetate, for luminescence, ≥99.0% (calc. on dry substance, T), ammonium bicarbonate, ≥99.5% (T), ammonium citrate dibasic, ≥99.0% (T), ammonium formate solution, 10 M in $H_2O$, ammonium formate, ≥99.0% (calc. based on dry substance, NT), ammonium oxalate monohydrate, ≥99.5% (RT), ammonium phosphate dibasic solution, 2.5 M in $H_2O$, ammonium phosphate dibasic, ≥99.0% (T), ammonium phosphate monobasic solution, 2.5 M in $H_2O$, ammonium phosphate monobasic, ≥99.5% (T), ammonium sodium phosphate dibasic tetrahydrate, ≥99.5% (NT), ammonium sulfate solution, for molecular biology, 3.2 M in $H_2O$, ammonium tartrate dibasic solution, 2 M in $H_2O$ (colorless solution at 20° C.), ammonium tartrate dibasic, ≥99.5% (T), BES buffered saline, for molecular biology, 2× concentrate, BES, ≥99.5% (T), BES, for molecular biology, ≥99.5% (T), BICINE buffer solution, for molecular biology, 1 M in H2O, BICINE, ≥99.5% (T), BIS-TRIS, ≥99.0% (NT), bicarbonate buffer solution, >0.1 M $Na_2CO_3$, >0.2 M $NaHCO_3$, boric acid, ≥99.5% (T), boric acid, for molecular biology, ≥99.5% (T), CAPS, ≥99.0% (TLC), CHES, ≥99.5% (T), calcium acetate hydrate, ≥99.0% (calc. on dried material, KT), calcium carbonate, precipitated, ≥99.0% (KT), calcium citrate tribasic tetrahydrate, ≥98.0% (calc. on dry substance, KT), citrate concentrated solution, for molecular biology, 1 M in $H_2O$, citric acid, anhydrous, ≥99.5% (T), citric acid, for luminescence, anhydrous, ≥99.5% (T), diethanolamine, ≥99.5% (GC), EPPS, ≥99.0% (T), ethylenediaminetetraacetic acid disodium salt dihydrate, for molecular biology, ≥99.0% (T), formic acid solution, 1.0 M in $H_2O$, Gly-Gly-Gly, ≥99.0% (NT), Gly-Gly, ≥99.5% (NT), glycine, ≥99.0% (NT), glycine, for luminescence, ≥99.0% (NT), glycine, for molecular biology, ≥99.0% (NT), HEPES buffered saline, for molecular biology, 2× concentrate, HEPES, ≥99.5% (T), HEPES, for molecular biology, ≥99.5% (T), imidazole buffer solution, 1 M in $H_2O$, imidazole, ≥99.5% (GC), imidazole, for luminescence, ≥99.5% (GC), imidazole, for molecular biology, ≥99.5% (GC), lipoprotein refolding buffer, lithium acetate dihydrate, ≥99.0% (NT), lithium citrate tribasic tetrahydrate, ≥99.5% (NT), MES hydrate, ≥99.5% (T), MES monohydrate, for luminescence, ≥99.5% (T), MES solution, for molecular biology, 0.5 M in $H_2O$, MOPS, ≥99.5% (T), MOPS, for luminescence, ≥99.5% (T), MOPS, for molecular biology, ≥99.5% (T), magnesium acetate solution, for molecular biology, ~1 M in $H_2O$, magnesium acetate tetrahydrate, ≥99.0% (KT), magnesium citrate tribasic nonahydrate, 98.0% (calc. based on dry substance, KT), magnesium formate solution, 0.5 M in $H_2O$, magnesium phosphate dibasic trihydrate, 98.0% (KT), neutralization solution for the in-situ hybridization for in-situ hybridization, for molecular biology, oxalic acid dihydrate, ≥99.5% (RT), PIPES, ≥99.5% (T), PIPES, for molecular biology, 99.5% (T), phosphate buffered saline, solution (autoclaved), phosphate buffered saline, washing buffer for peroxidase conjugates in western blotting, 10× concentrate, piperazine, anhydrous, ≥99.0% (T), potassium D-tartrate monobasic, ≥99.0% (T), potassium acetate solution, for molecular biology, potassium acetate solution, for molecular biology, 5 M in $H_2O$, potassium acetate solution, for molecular biology, ~1 M in $H_2O$, potassium acetate, ≥99.0% (NT), potassium acetate, for luminescence, ≥99.0% (NT), potassium acetate, for molecular biology, ≥99.0% (NT), potassium bicarbonate, 99.5% (T), potassium carbonate, anhydrous, ≥99.0% (T), potassium chloride, ≥99.5% (AT), potassium citrate monobasic, ≥99.0% (dried material, NT), potassium citrate tribasic solution, 1 M in $H_2O$, potassium formate solution, 14 M in $H_2O$, potassium formate, ≥99.5% (NT), potassium oxalate monohydrate, ≥99.0% (RT), potassium phosphate dibasic, anhydrous, ≥99.0% (T), potassium phosphate dibasic, for luminescence, anhydrous, ≥99.0% (T), potassium phosphate dibasic, for molecular biology, anhydrous, ≥99.0% (T), potassium phosphate monobasic, anhydrous, ≥99.5% (T), potassium phosphate monobasic, for molecular biology, anhydrous, ≥99.5% (T), potassium phosphate tribasic monohydrate, 95% (T), potassium phthalate monobasic, 99.5% (T), potassium sodium tartrate solution, 1.5 M in $H_2O$, potassium sodium tartrate tetrahydrate, ≥99.5% (NT), potassium tetraborate tetrahydrate, ≥99.0% (T), potassium tetraoxalate dihydrate, ≥99.5% (RT), propionic acid solution, 1.0 M in $H_2O$, STE buffer solution, for molecular biology, pH 7.8, STET buffer solution, for molecular biology, pH 8.0, sodium 5,5-diethylbarbiturate, ≥99.5% (NT), sodium acetate solution, for molecular biology, ~3 M in $H_2O$, sodium acetate trihydrate, ≥99.5% (NT), sodium acetate, anhydrous, ≥99.0% (NT), sodium acetate, for luminescence, anhydrous, 99.0% (NT), sodium acetate, for molecular biology, anhydrous, ≥99.0% (NT), sodium bicarbonate, ≥99.5% (T), sodium bitartrate monohydrate, ≥99.0% (T), sodium carbonate decahydrate, ≥99.5% (T), sodium carbonate, anhydrous, ≥99.5% (calc. on dry substance, T), sodium citrate monobasic, anhydrous, ≥99.5% (T), sodium citrate tribasic dihydrate, ≥99.0% (NT), sodium citrate tribasic dihydrate, for luminescence, 99.0% (NT), sodium citrate tribasic dihydrate, for molecular biology, ≥99.5% (NT), sodium formate solution, 8 M in $H_2O$, sodium oxalate, ≥99.5% (RT), sodium phosphate dibasic dihydrate, ≥99.0% (T), sodium phosphate dibasic dihydrate, for luminescence, 99.0% (T), sodium phosphate dibasic dihydrate, for molecular biology, ≥99.0% (T), sodium phosphate dibasic dodecahydrate, ≥99.0% (T), sodium phosphate dibasic solution, 0.5 M in $H_2O$, sodium phosphate dibasic, anhydrous, ≥99.5% (T), sodium phosphate dibasic, for molecular biology, ≥99.5% (T), sodium phosphate monobasic dihydrate, ≥99.0% (T), sodium phosphate monobasic dihydrate, for molecular biology, 99.0% (T), sodium phosphate monobasic monohydrate, for molecular biology, 99.5% (T), sodium phosphate monobasic solution, 5 M in $H_2O$, sodium pyrophosphate dibasic, ≥99.0% (T), sodium pyrophosphate tetrabasic decahydrate, ≥99.5% (T), sodium tartrate dibasic dihydrate, ≥99.0% (NT), sodium tartrate dibasic solution, 1.5 M in $H_2O$ (colorless solution at 20° C.), sodium tetraborate decahydrate, ≥99.5% (T), TAPS, ≥99.5% (T), TES, ≥99.5% (calc. based on dry substance, T), TM buffer solution, for molecular biology, pH 7.4, TNT buffer solution, for molecular biology, pH 8.0, TRIS glycine buffer solution, 10× concentrate, TRIS acetate-EDTA buffer solution, for molecular biology, TRIS buffered saline, 10× concentrate, TRIS glycine SDS buffer solution, for electrophoresis, 10× concentrate, TRIS phosphate-EDTA buffer solution, for molecular biology, concentrate, 10× concentrate, tricine, ≥99.5% (NT), triethanolamine, ≥99.5% (GC), triethylamine, ≥99.5% (GC), triethylammonium acetate buffer, volatile buffer, ~1.0 M in H$_2$O, triethylammonium phosphate solution, volatile buffer, ~1.0 M in H$_2$O, trimethylammonium acetate solution, volatile buffer, ~1.0 M in H$_2$O, trimethylammonium phosphate solution, volatile buffer, ~1 M in H$_2$O, TRIS-EDTA buffer solution, for molecular biology, concentrate, 100× concentrate, TRIS-EDTA buffer solution, for molecular biology, pH 7.4, TRIS-EDTA buffer solution, for molecular biology, pH 8.0, TRIZMA acetate, ≥99.0% (NT), TRIZMA base, ≥99.8% (T), TRIZMA base, ≥99.8% (T), TRIZMA base, for luminescence, ≥99.8% (T), TRIZMA base, for molecular biology, ≥99.8% (T), TRIZMA carbonate, ≥98.5% (T), TRIZMA hydrochloride buffer solution, for molecular biology, pH 7.2, TRIZMA hydrochloride buffer solution, for molecular biology, pH 7.4, TRIZMA hydrochloride buffer solution, for molecular biology, pH 7.6, TRIZMA hydrochloride buffer solution, for molecular biology, pH 8.0, TRIZMA hydrochloride, ≥99.0% (AT), TRIZMA hydrochloride, for luminescence, ≥99.0% (AT), TRIZMA hydrochloride, for molecular biology, ≥99.0% (AT), and TRIZMA maleate, ≥99.5% (NT).

(II) Pharmaceutical Compositions

Another aspect of the present disclosure encompasses formulating a composition of the invention comprising a nanoemulsion into a pharmaceutical composition and then administering the pharmaceutical composition to a subject. In some aspects the pharmaceutical composition induces an immune response. In other aspects the pharmaceutical composition is a vaccine.

(a) Composition

In an embodiment, the nanoemulsion may be formulated into a pharmaceutical composition of the invention in a therapeutically effective amount and suitable, pharmaceutically-acceptable excipient(s) for administration to a subject.

In an embodiment, the pharmaceutically-acceptable excipient(s) may include binders, diluents (fillers), disintegrants, effervescent disintegration agents, preservatives (antioxidants), flavor-modifying agents, lubricants and glidants, dispersants, coloring agents, pH modifiers, chelating agents, antimicrobial agents, release-controlling polymers, and combinations of any of these agents.

(i) Binder

Suitable binders include, without limit, starches, pregelatinized starches, gelatin, polyvinylpyrolidone, cellulose, methylcellulose, sodium carboxymethylcellulose, ethylcellulose, polyacrylam ides, polyvinyloxoazolidone, polyvinyl-alcohols, C$_{12}$-C$_{18}$ fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons.

In one embodiment, a binder may be introduced into the mixture to be granulated in a solid form, without limit, a crystal, a particle, a powder, or any other finely divided solid form known in the art. In another embodiment, the binder may be dissolved or suspended in a solvent and sprayed onto the mixture in a granulation device as a binder fluid during granulation.

(ii) Diluent

Suitable diluents include, without limit, carbohydrates, inorganic compounds, biocompatible polymers, e.g., polyvinylpyrrolidone (PVP), dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, saccharides such as sucrose, dextrose, lactose, microcrystalline cellulose, fructose, xylitol, and sorbitol, polyhydric alcohols, starches, pre-manufactured direct compression diluents, and mixtures thereof.

(iii) Disintegrant

Disintegrates include, without limit, non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include, without limit, sodium bicarbonate in combination with citric acid, and sodium bicarbonate in combination with tartaric acid.

(iv) Preservatives

Suitable preservatives include, without limit, ascorbic acid and its salts, ascorbyl palm itate, ascorbyl stearate, anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, cetyl gallate, chlorogenic acid, citric acid and its salts, clove extract, coffee bean extract, p-coumaric acid, 3,4-dihydroxybenzoic acid, N,N'-diphenyl-p-phenylenediam ine (DPPD), dilauryl thiodipropionate, distearyl thiodipropionate, 2,6-di-tert-butylphenol, dodecyl gallate, edetic acid, ellagic acid, erythorbic acid, sodium erythorbate, esculetin, esculin, 6-ethoxy-1,2-dihydro-2,2,4-trimethylquinoline, ethyl gallate, ethyl maltol, ethylenediaminetetraacetic acid (EDTA), eucalyptus extract, eugenol, ferulic acid, flavonoids (e.g., catechin, epicatechin, epicatechin gallate, epigallocatechin (EGC), epigallocatechin gallate (EGCG), polyphenol epigallocatechin-3-gallate), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinic acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, methyl gallate, monoglyceride citrate; monoisopropyl citrate; morin, beta-naphthoflavone, nordihydroguaiaretic acid (NDGA), octyl gallate, oxalic acid, palmityl citrate, phenothiazine, phosphatidylcholine, phosphoric acid, phosphates, phytic acid, phytylubichromel, pimento extract, propyl gallate, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., lonox 100), 2,4-(tris-3',5'-bi-tert-butyl-4'-hydroxybenzyl)-mesitylene (i.e., lonox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof. In an exemplary embodiment, the preservatives is an antioxidant, such as a-tocopherol or ascorbate, and antimicrobials, such as parabens, chlorobutanol or phenol.

(v) Lubricants

Lubricants may be utilized to lubricate ingredients that form a pharmaceutical composition. As a glidant, the lubricant facilitates removal of solid dosage forms during the manufacturing process. Lubricants and glidants include, without limit, magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil. The pharmaceutical composition will generally comprise from about 0.01% to about 10% by weight of a lubricant. In some embodiments, the pharmaceutical composition will comprise from about 0.1% to about 5% by weight of a lubricant. In a further embodiment, the pharmaceutical composition will comprise from about 0.5% to about 2% by weight of a lubricant.

(vi) Dispersants

Dispersants include, without limit, starch, alginic acid, polyvinylpyrrolidones, guar gum, kaolin, bentonite, purified wood cellulose, sodium starch glycolate, isoamorphous silicate, and microcrystalline cellulose as high hydrophilic-lipophilic balance (HLB) emulsifier surfactants.

(vii) pH Modifers pH modifiers include, without limit, citric acid, acetic acid, tartaric acid, malic acid, fumaric acid, lactic acid, phosphoric acid, sorbic acid, benzoic acid, sodium carbonate, and sodium bicarbonate.

(viii) Coloring Agent

Depending upon the formulation, it may be desirable to include a coloring agent. Suitable color additives include, without limit, food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in various embodiments.

(ix) Chelating Agent

A chelating agent may include an excipient to immobilize oxidative groups, without limit, metal ions, in order to inhibit the oxidative degradation of the morphinan by these oxidative groups. Suitable chelating agents include, without limit, lysine, methionine, glycine, gluconate, polysaccharides, glutamate, aspartate, and disodium ethylenediaminetetraacetate ($Na_2EDTA$).

(x) Antimicrobial Agent

An antimicrobial agent may be included as an excipient to minimize the degradation of the nanoemulsion according to this disclosure by microbial agents, include, without limit, bacteria and fungi. Antimicrobials include, without limit, parabens, chlorobutanol, phenol, calcium propionate, sodium nitrate, sodium nitrite, $Na_2EDTA$, and sulfites including, without limit, sulfur dioxide, sodium bisulfite, and potassium hydrogen sulfite.

(b) Administration (i) Dosage Forms

In an embodiment, the composition of the invention may be formulated into a dosage form for pharmaceutical administration. Suitable dosage forms include, without limit, liquids, ointments, creams, emulsions, lotions, gels, bioadhesive gels, sprays, aerosols, pastes, foams, sunscreens, capsules, microcapsules, suspensions, pessary, powder, semi-solid dosage form, etc. In some embodiments, the composition of the invention may be formulated into a liquid dispersion, gel, aerosol, nasal aerosol, ointment, cream, semi-solid, or suspension. In preferred embodiments, the composition of the invention may be formulated into a nasal aerosol.

In an embodiment, internasal administration includes administration via the nose, either with or without concomitant inhalation during administration. Such administration is typically through contact by the composition of the invention comprising the nanoemulsion with the nasal mucosa, nasal turbinates or sinus cavity. Administration by inhalation comprises intranasal administration, or may include oral inhalation. Such administration may also include contact with the oral mucosa, bronchial mucosa, and other epithelia.

In an embodiment, the composition of the invention may be formulated for immediate release, sustained release, controlled release, delayed release, or any combinations thereof, into the epidermis or dermis. In some embodiments, the composition of the invention may comprise a penetration-enhancing agent. Suitable penetration-enhancing agents include, without limit, alcohols such as ethanol, triglycerides and aloe compositions. The amount of the penetration-enhancing agent may comprise from about 0.5% to about 40% by weight of the formulation.

(ii) Dosage

In an embodiment, the composition of the invention may be formulated into a pharmaceutical composition in a therapeutically effective amount. In an embodiments, the therapeutically effective amount can and will vary depending on the subject. In an embodiment, the therapeutically effective amount may be from about 1 µL to about 50 µL. In some embodiments, the therapeutically effective amount may be about 1 µL, about 2 µL, about 3 µL, about 4 µL, about 5 µL, about 6 µL, about 7 µL, about 8 µL, about 9 µL, about 10 µL, about 11 µL, about 12 µL, about 13 µL, about 14 µL, about 15 µL, about 16 µL, about 17 µL, about 18 µL, about 19 µL, about 20 µL, about 21 µL, about 22 µL, about 23 µL, about 24 µL, about 25 µL, about 26 µL, about 27 µL, about 28 µL, about 29 µL, about 30 µL, about 31 µL, about 32 µL, about 33 µL, about 34 µL, about 35 µL, about 36 µL, about 37 µL, about 38 µL, about 39 µL, about 40 µL, about 41 µL, about 42 µL, about 43 µL, about 44 µL, about 45 µL, about 46 µL, about 47 µL, about 48 µL, about 49 µL, or about 50 µL.

In an embodiment, it is expected that each dose of a composition of the invention comprising a nanoemulsion comprises about 1% (v/v) to about 40% (v/v) nanoemulsion. In some embodiments, each dose of a pharmaceutical composition comprising a nanoemulsion comprises about 1% (v/v), about 2% (v/v), about 3% (v/v), about 4% (v/v), about 5% (v/v), about 6% (v/v), about 7% (v/v), about 8% (v/v), about 9% (v/v), about 10% (v/v), about 11% (v/v), about 12% (v/v), about 13% (v/v), about 14% (v/v), about 15% (v/v), about 16% (v/v), about 17% (v/v), about 18% (v/v), about 19% (v/v), about 20% (v/v), about 21% (v/v), about 22% (v/v), about 23% (v/v), about 24% (v/v), about 25% (v/v), about 26% (v/v), about 27% (v/v), about 28% (v/v), about 29% (v/v), about 30% (v/v), about 31% (v/v), about 32% (v/v), about 33% (v/v), about 34% (v/v), about 35% (v/v), about 36% (v/v), about 37% (v/v), about 38% (v/v), about 39% (v/v) or about 40% (v/v) nanoemulsion.

In an embodiment, it is expected that each dose of a composition of the invention comprising a nanoemulsion comprises about 10 µg to about 50 µg of the at least one isolated *Mycobacterium tuberculosis* antigen, or an antigenic fragment thereof. In some embodiments, each dose of a pharmaceutical composition comprising a nanoemulsion comprises about 10 µg, about 15 µg, about 20 µg, about 25 µg, about 30 µg, about 35 µg, about 40 µg, about 45 µg, or about 50 µg of the at least one isolated *Mycobacterium tuberculosis* antigen, or an antigenic fragment thereof. In a preferred embodiment, each dose of a pharmaceutical composition comprising a nanoemulsion comprises about 25 µg of the at least one isolated *Mycobacterium tuberculosis* antigen, or an antigenic fragment thereof.

(iii) Frequency

In an embodiment, following an initial administration of the composition of the invention, a subject may receive one or more boost administrations. In some embodiments, the one or more boost administrations may be administered at about 1 day, about 2 days, about 3 days, about 5 days, about 6 days, about 1 week, about 2 weeks, about 3 weeks, about 4 weeks, about 5 weeks, about 6 weeks, about 6 weeks, about 8 weeks, about 9 weeks, about 10 weeks, about 3 months, about 4 months, about 6 months, about 9 months, about 1 year, about 2 years, about 3 years, about 5 years, or about 10 years subsequent to a first, second, third, fourth, fifth, sixth, seventh, eighth, ninth, tenth, and/or more than tenth initial administration.

(iv) Subject

A suitable subject includes a human, a livestock animal, a companion animal, a lab animal, or a zoological animal. In one embodiment, the subject may be a rodent, e.g., a mouse, a rat, a guinea pig, etc. In another embodiment, the subject may be a livestock animal. Non-limiting examples of suitable livestock animals may include pigs, cows, horses, goats, sheep, llamas and alpacas. In yet another embodiment, the subject may be a companion animal. Non-limiting examples of companion animals may include pets such as dogs, cats, rabbits, and birds. In yet another embodiment, the subject may be a zoological animal. As used herein, a "zoological animal" refers to an animal that may be found in a zoo. Such animals may include non-human primates, large cats, wolves, and bears. In a specific embodiment, the animal is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the subject is a human.

(III) Immune Response

Another aspect of the present disclosure encompasses eliciting an immune response following administration of a composition of the invention comprising a nanoemulsion and at least one isolated mycobacterial antigen, or an antigenic fragment thereof. As used herein, "immune response" refers to an alteration of the subjects' immune system after administration of a composition of the invention. In certain embodiments, a composition of the invention can elicit a cellular immune response, i.e., Th1 and Th17 responses.

A cellular immune response is mediated by T-lymphocytes and involves production of cytotoxic T-lymphocytes, activated macrophages, activated Natural Killer cells, and secretion of cytokines. Among the T-lymphocytes, CD4+ T cells have the ability to proliferate and differentiate into T helper cells responsive to specific antigens. Sub-populations of T helper cells are classified by the cytokines they produce. Th17 cells notably produce cytokines, e.g., interleukin-17. Interleukin-17 in turn stimulates stromal cells to release inflammatory cytokines such as IL-8 and IL-6, which function as chemo-attractants for neutrophils and macrophages.

(i) Cytokines

In an embodiment, an immune response in a subject can be measured by determining the titer of cytokines. In some embodiments, the cytokines may include a member of the α-helix bundle family, IL-1 family, IL-17 family, and cysteine-knot cytokines. The α-helix bundle family may include members of the IL-2 subfamily, interferon (IFN) subfamily, and/or the IL-10 subfamily. Suitable members of the IL-2 subfamily may include, without limit, IL-2, IL-4, IL-7, IL-9, IL-15, and IL-21. Suitable members of the interferon (IFN) subfamily may include, without limit, INF-α, INF-β, INF-ε, INF-κ, INF-ω, IL10R2, and IFNLR1. Suitable members of the IL-10 subfamily include, without limit, IL-19, IL-20, IL-22, IL-24 (Mda-7), IL-26, IL-28A, IL-28B, and IL-29. Suitable members of the IL-1 family include, without limit IL-1a, IL-1B, IL-1Ra, IL-18, IL-36Ra, IL-36α, IL-37, IL-36β, IL-36γ, IL-38, and IL-33. Suitable members of the IL-17 family include, without limit, IL-17B, IL-17C, IL-17D, IL-17E, and IL-17F. Suitable members of the cysteine-knot cytokines include, without limit, TGF-β1, TGF-β2, and TFG-β3. In preferred embodiments, the cytokines include IFN γ, IL-17, and a combination thereof.

In an embodiment, the cytokines may be detected using Western blotting or an enzyme-linked immunosorbent (ELISA) assay A person skilled in the art would be able to select and use the appropriate detection method.

(IV) Screening Platform

An aspect of the present disclosure is directed to a method of screening a composition of the invention for an immune response. The method comprises (i) administering the composition to be screened to a screening platform; (ii) infecting the screening platform with a strain of mycobacteria; (iii) measuring the immune response in the screening platform; (iv) comparing the immune response of the screening platform in step (iii) to a control screen platform that was not administered the composition; wherein, if there is a difference, the composition elicits an immune response. In another aspect of the present disclosure, methods directed to screening a composition of the invention for an immune response may additionally include administering dendritic cells to the screening platform before, after or at the time of infecting the screening platform with a strain of mycobacteria.

(i) Screening Platform

As used herein, "screening platform" refers to a model system that can be used to assess immune response(s) to administration of a complete, incomplete, partial formulation of a composition of the invention. In an embodiment, a screening platform may include bacteria, yeast, a single mammalian cell, multiple mammalian cells, a tissue, an organ, blood, a subject as defined herein. In a specific embodiment, the screening platform is a laboratory animal. Non-limiting examples of a laboratory animal may include rodents, canines, felines, and non-human primates. In certain embodiments, the animal is a rodent. Non-limiting examples of rodents may include mice, rats, guinea pigs, etc. In preferred embodiments, the screening platform is a mouse.

In an embodiment, a screening platform yields immune response(s) for assessment of administered composition of the invention or components thereof. Non-limiting examples of immune responses assessed by the screening platform may include alterations of phagocytes, T-cells, cytokines. An immune response may be an increase, a decrease, acceleration, an ablation, a delay in the rate of activation of phagocytes in response to administration of a composition of the invention or components thereof, independent of T-cell and/or cytokine response. An immune response may be an increase, a decrease, acceleration, an ablation, a delay in the rate of activation of T-cells in response to administration of a composition of the invention or components thereof, independent of phagocyte and/or cytokine response. An immune response may be an increase, a decrease, acceleration, an ablation, a delay in the rate of activation of cytokines in response to administration of a composition of the invention or components thereof, independent of phagocyte and/ or T-cell response. In certain embodiments, an immune response is a T-cell response. In preferred embodiments, an immune response is a T cell response delay.

In an embodiment, immune response(s) to administration of a composition of the invention or components thereof may be used to assess functionality of the composition or components thereof. In another embodiment, assessments of functionality may include adjuvant response, antigen response, adjuvant-modulated antigen response, stability, safety, dose response, efficacy. In preferred embodiments, immune response(s) to administered compositions of the invention or components thereof assess efficacy. In an embodiment, efficacy is at least a 95%, at least a 90%, at least a 85%, at least a 80%, at least a 75%, at least a 70%, at least a 65%, at least a 60%, at least a 55%, at least a 50%, at least a 45%, at least a 40%, at least a 35%, at least a 30%, at least a 25%, at least a 20%, at least a 15%, at least a 10%, at least a 5% immune response in a treated screening platform compared to an untreated, control screening platform. In another embodiment, efficacy is at least a 95%, at least a 90%, at least a 85%, at least a 80%, at least a 75%, at least a 70%, at least a 65%, at least a 60%, at least a 55%, at least a 50%, at least a 45%, at least a 40%, at least a 35%, at least a 30%, at least a 25%, at least a 20%, at least a 15%, at least a 10%, at least a 5% T-cell response in a treated screening platform at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days following infection compared to an untreated, control screening platform. In certain embodiments, efficacy is at least a 95%, at least a 90%, at least a 85%, at least a 80%, at least a 75%, at least a 70%, at least a 65%, at least a 60%, at least a 55%, at least a 50%, at least a 45%, at least a 40%, at least a 35%, at least a 30%, at least a 25%, at least a 20%, at least a 15%, at least a 10%, at least a 5% increase in T-cell response in a treated screening platform at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days following infection compared to an untreated, control screening platform. In certain embodiments, efficacy is at least a 95%, at least a 90%, at least a 85%, at least a 80%, at least a 75%, at least a 70%, at least a 65%, at least a 60%, at least a 55%, at least a 50%, at least a 45%, at least a 40%, at least a 35%, at least a 30%, at least a 25%, at least a 20%, at least a 15%, at least a 10%, at least a 5% delay of T-cell response in a treated screening platform at least 1 day, at least 2 days, at least 3 days, at least 4 days, at least 5 days, at least 6 days, at least 7 days, at least 8 days, at least 9 days, at least 10 days, at least 11 days, at least 12 days, at least 13 days, at least 14 days, at least 15 days, at least 16 days, at least 17 days, at least 18 days, at least 19 days, at least 20 days, at least 21 days following infection compared to an untreated, control screening platform.

In an embodiment, administration of a complete, incomplete, partial formulation of a composition of the invention administered to a screening platform evokes immune response(s). In an embodiment, at least a nanoemulsion, at least an adjuvant, at least an antigen, at least an antigen fragment, at least a composition is administered to the screening platform. In certain embodiments, a composition of the invention is administered. In some embodiments, the composition of the invention is a vectored composition, a subunit composition, a recombinant composition. In an embodiment, a composition of the invention that may be administered is a known vaccine. Non-limiting examples of known vaccines may include bacilli Calmette-Guérin (BCG), modified vaccinia Ankara 85A (MVA85A), recombinant *Bacillus* Calmette-Guérin 30 (rBCG30), 72F fusion protein vaccine, ESAT6-Ag85b fusion protein vaccine. In some embodiments, the composition of the invention is against mycobacteria. In some embodiments, the composition of the invention against *mycobacterium* is against a mycobacterial strain selected from the group consisting of: *Mycobacterium avium* complex (MAC), *Mycobacterium kansasii, Mycobacterium xenopi, Mycobacterium marinum, Mycobacterium ulcerans*, the *Mycobacterium fortuitum* complex (*Mycobacterium fortuitum, Mycobacterium abscessus,* and *Mycobacterium chelonae*), *Mycobacterium gordonae, Mycobacterium abscessus,* and *Mycobacterium tuberculosis* complex ((MTBC) *Mycobacterium africanum, Mycobacterium bovis, Mycobacterium canetti, Mycobacterium caprae, Mycobacterium microti, Mycobacterium mungi, Mycobacterium orygis, Mycobacterium pinnipedii, Mycobacterium suricattae, Mycobacterium tuberculosis*).

(ii) Method

In an embodiment, methods of screening a compositions of the invention for an immune response are comprised of (i) administering the composition to be screened to a screening platform; (ii) infecting the screening platform with a strain of mycobacteria; (iii) measuring the immune response in the screening platform; (iv) comparing the immune response of the screening platform in step (iii) to a control screening platform that was not administered the composition; wherein if there is a difference, the composition elicits an immune response. As used herein, "a control screening platform" is identical to a screening platform with provision that a composition of the invention is not administered. In another embodiment, a method of screening a composition of the invention for an immune response comprises (i) administering the composition to be screened to a screening platform; (ii) infecting the screening platform with a strain of mycobacteria; (iii) measuring the immune response in the screening platform; (iv) comparing the immune response of the screening platform in step (iii) to a control screening platform that was not administered the composition; wherein, dendritic cells can be administered before, after, or simultaneously at the time of infection; wherein if there is a difference in immune response between the screening platform in step (iii) and the control screening platform, the composition elicits an immune response.

In an embodiment, a composition of the invention or components thereof may be administered to a screening platform by route of administration known in the art. Non-limiting examples include endosinusial, endotracheal, transtracheal, intratracheal, intrabronchial, intracavernous, intrapleural, intrapulmonary, intrasinal, nasal, oral, parenteral, inhalation, subcutaneous, submucosal, mucosal, transmucosal. In another embodiment, a composition of the invention or components thereof may be administered to a vaccinated screening platform at least 1 day, at least 3 days, at least 5 days, at least 1 week, at least 3 weeks, at least 4 weeks, at least 2 months, at least 4 months, at least 8 months, at least one year after a first administration of a composition of the invention. In another embodiment, a composite of the invention or components thereof may be administered to a boosted screening platform at least one additional dose, at least 2 additional doses, at least 3 additional doses wherein at least 1 day, at least 3 days, at least 5 days, at least 1 week, at least 3 weeks, at least 4 weeks, at least 2 months, at least 4 months, at least 8 months, at least one year separates the time between doses.

In an embodiment, the screening platform is infected with mycobacteria. In an embodiment, the strain is a *mycobacterium*. In some embodiments, the strain of *Mycobacterium* selected from the group consisting of: *Mycobacterium avium* complex (MAC), *Mycobacterium kansasii, Mycobacterium xenopi, Mycobacterium marinum, Mycobacterium ulcerans,* the *Mycobacterium fortuitum* complex (*Mycobacterium fortuitum, Mycobacterium abscessus,* and *Mycobacterium chelonae*), *Mycobacterium gordonae, Mycobacterium abscessus,* and *Mycobacterium tuberculosis* complex ((MTBC) *Mycobacterium africanum, Mycobacterium bovis, Mycobacterium canetti, Mycobacterium caprae, Mycobacterium microti, Mycobacterium mungi, Mycobacterium orygis, Mycobacterium pinnipedii, Mycobacterium suricattae, Mycobacterium tuberculosis*). In a preferred embodiment, the strain is *Mycobacterium tuberculosis*. The strain may be administered to a screening platform by route of administration known in the art. Non-limiting examples include endosinusial, endotracheal, transtracheal, intratracheal, intrabronchial, intracavernous, intrapleural, intrapulmonary, intrasinal, nasal, oral, parenteral, inhalation, subcutaneous, submucosal, mucosal, transmucosal. In another embodiment, a strain may be administered to a screening platform at least 1 day, at least 3 days, at least 5 days, at least 1 week, at least 3 weeks, at least 4 weeks, at least 2 months, at least 4 months, at least 8 months, at least one year after a first administration of a composition of the invention. In another embodiment, a strain may be administered to a screening platform at least 1 day, at least 3 days, at least 5 days, at least 1 week, at least 3 weeks, at least 4 weeks, at least 2 months, at least 4 months, at least 8 months, at least one year after the last vaccination boost is administered. In an embodiment, at least 50, at least 100, at least 150, at least 200, at least 300, at least 400, at least 500, at least 750, at least 1000 colony-forming units (CFU) of strain are administered to a screening platform.

Methods described herein to assess immune responses following administration of a composition of the invention be according to a variety of standard techniques known to the art. A person skilled in the art would be able to select and use the appropriate detection method. In certain embodiments, methods to assess immune responses are directed to measuring T cell responses. In preferred embodiments, methods to assess T cell responses are directed to measuring the accumulation of T cells in the screening platform. Non-limiting examples of methods that may be used to measure accumulation of T cells in a sample include measuring bacterial burden in the lung by plating, measuring $CD4^+$ T cell accumulation and activation of macrophages. Non-limiting examples of methods that may be used to measure $CD4^+$ T cell accumulation and activation of macrophages include detecting CD44 expression on $CD3^+CD4^+$ T cells, measuring IL-17 and IFN-γ production by Ag85B-specific $CD4^+CD44^{hi}$ T cells, and detecting MHC-II mean fluorescence intensity (MFI) on lung alveolar macrophages.

In an embodiment, the immune response is measured at least 1 day post infection (dpi), at least 2 days dpi, at least 3 days dpi, at least 4 days dpi, at least 5 days dpi, at least 6 days dpi, at least 7 days dpi, at least 8 days dpi, at least 9 days dpi, at least 10 days dpi, at least 11 days dpi, at least 12 days dpi, at least 13 days dpi, at least 14 days dpi, at least 15 days dpi, at least 16 days dpi, at least 17 days dpi, at least 18 days dpi, at least 19 days dpi, at least 20 days dpi, at least 21 days dpi. In another embodiment, the immune response is measured between at least 1 and at least 21 days dpi, between at least 1 and at least 10 days dpi, between at least 10 and at least 21 days dpi.

In an embodiment, the immune response is assessed to determine functionality of an administered composition of the invention or components thereof. In certain embodiment, the immune response is assessed to determine the efficacy of a composition of the invention. In a preferred embodiment, a T cell response following administration of composition of the invention comprising a nanoemulsion and at least one isolated mycobacterial antigen, or an antigenic fragment thereof to a screening platform is compared to a control screening platform to determine efficacy.

In an optional embodiment, dendritic cells (DCs) may be administered to a screening platform following the final vaccination boost. In an embodiment, DCs may be administered before, after, or simultaneously with administration of *Mycobacterium* strain to infect the screen platform. In another embodiment, DCs may be administered at least once, at least twice, at least three-times after the initial administration. In an embodiment, the time between each DC administration is at least one day, at least two days, at least three days, at least 4 days, at least 8 days, at least 20 days. In an embodiment, DCs may be administered to a screening platform by route of administration known in the art. Non-limiting examples include endosinusial, endotracheal, transtracheal, intratracheal, intrabronchial, intracavernous, intrapleural, intrapulmonary, intrasinal, nasal, oral, parenteral, inhalation, subcutaneous, submucosal, mucosal, transmucosal. In an embodiment, DCs are administered at least $1\times10^4$ cells, at least $1\times10^5$ cells, at least $1\times10^6$ cells, at least $1\times10^7$ cells, at least $1\times10^8$ cells per dose.

In another embodiment, DCs may be pulsed with a protein, a peptide, an antigen, or may be RNA-transfected to yield "primed DCs," as referred to herein. In yet another embodiment, DCs and primed DCs may be stimulated with chemicals, antibodies, oligodeoxynucleotides to yield "activated DCs" and "activated-primed DCs" as referred to herein. In preferred embodiments, DCs are activated with amphiphilic-CpG (amph-CpG), CD40 ligation, TNF-α ligation, zymosan, and/or FGK4.5.

Definitions

The term "nanoemulsion," as used herein, includes dispersions or droplets, as well as other lipid structures that can form as a result of hydrophobic forces that drive apolar residues (i.e., long hydrocarbon chains) away from water and drive polar head groups toward water, when a water immiscible oily phase is mixed with an aqueous phase. These other lipid structures include, without limit, unilamellar, paucilamellar, and multilamellar lipid vesicles, micelles, and lamellar phases.

The term "surfactant" refers to any molecule having both a polar head group, which energetically prefers solvation by water, and a hydrophobic tail which is not well solvated by water. The term "cationic surfactant" refers to a surfactant with a cationic head group. The term "anionic surfactant" refers to a surfactant with an anionic head group. The term "non-ionic surfactant: refers to a surfactant with uncharged head groups. The term "zwitterioninc surfactant refers to a surfactant with both cationic and anionic head groups.

The terms "pharmaceutically acceptable" or "pharmacologically acceptable," as used herein, refer to compositions that do not substantially produce adverse allergic or adverse immunological reactions when administered to a host, e.g., an animal or a human. Such formulations include any pharmaceutically acceptable dosage form. Examples of such pharmaceutically acceptable dosage forms include, without limit, dips, sprays, seed dressings, stem injections, lyophilized dosage forms, sprays, and mists. As used herein, "pharmaceutically acceptable carrier" includes any and all solvents, dispersion media, coatings, wetting agents, e.g., sodium lauryl sulfate, isotonic and absorption delaying agents, disintegrants, e.g., potato starch or sodium starch glycolate, and the like.

The term "intranasal(ly)," as used herein, refers to application of the compositions of the present invention to the surface of the skin and mucosal cells and tissues of the nasal passages, e.g., nasal mucosa, sinus cavity, nasal turbinates, or other tissues and cells which line the nasal passages. Intranasal administration includes administration via the nose, either with or without concomitant inhalation during administration. Such administration is typically through contact by the composition of the invention comprising the nanoemulsion with the nasal mucosa, nasal turbinates or sinus cavity. Administration by inhalation comprises intranasal administration, or may include oral inhalation. Such administration may also include contact with the oral mucosa, bronchial mucosa, and other epithelia.

The term "adjuvant," as used herein refers to a substance that assists or modifies the immunological action of a pharmaceutical composition, including, without limit, adjuvants that increase or diversify the immune response to an antigen. Typically, an "adjuvant" is a substance that enhances the immune response of a host organism to an antigen. Adjuvants are added to antigens when the required immune response is quantitatively and/or qualitatively different to that induced by the antigen alone, as is often the case when the antigen is being delivered as a vaccine to an animal or person. A substance is said to "enhance" an immune response of a host organism to an antigen, i.e., is an adjuvant, if the immune response experienced by the host organism is greater when an antigen is applied to the host organism, in combination with the putative adjuvant, compared to the immune response experienced by the host organism when an antigen is applied without the putative adjuvant. Various immune cell assays can give a good indication of whether a substance is likely to be an effective adjuvant in a host organism (See for example, U.S. Pat. No. 6,406,705, which cites measuring the antibody forming capacity and number of lymphocyte subpopulations using a mixed leukocyte response assay and lymphocyte proliferation assay).

The term "modified release formulation," as used herein refers to a composition that has a release profile of anything other than immediate release. Non-limiting examples include a controlled release formulation, a sustained release formulation, or any combination thereof or in combination with an immediate release formulation.

EXAMPLES

The following examples are included to demonstrate various embodiments of the present disclosure. It should be appreciated by those of skill in the art that the techniques disclosed in the examples that follow represent techniques discovered by the inventors to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Introduction for Examples 1-3

*Mycobacterium tuberculosis* (Mtb) latently infects one-third of the world's population, causing pulmonary tuberculosis (PTB) in ~9 million people and resulting in ~1.4 million deaths each year.[1] The currently available TB vaccine, *Mycobacterium bovis* BCG (BCG), shows variable efficacy in protection against PTB. In addition, multi-drug resistant (MDR) Mtb strains have recently emerged. Thus, there is a great need for new TB vaccines.[2] TB vaccine development during the past decade has focused on targeting interferon-gamma (IFN-γ) secretion from T helper 1 (Th1) cells to mediate early macrophage activation and bacterial killing.[3] A recombinant TB vaccine, MVA85A, was recently tested in human clinical trials. Despite inducing high levels of interferon gamma (IFN-γ) production from T cells,[4, 5] this vaccine failed to protect against TB disease. [6, 7] These data highlight the importance of exploring new and more effective immune approaches to improve vaccine-induced immunity against TB.

Figure 1B:
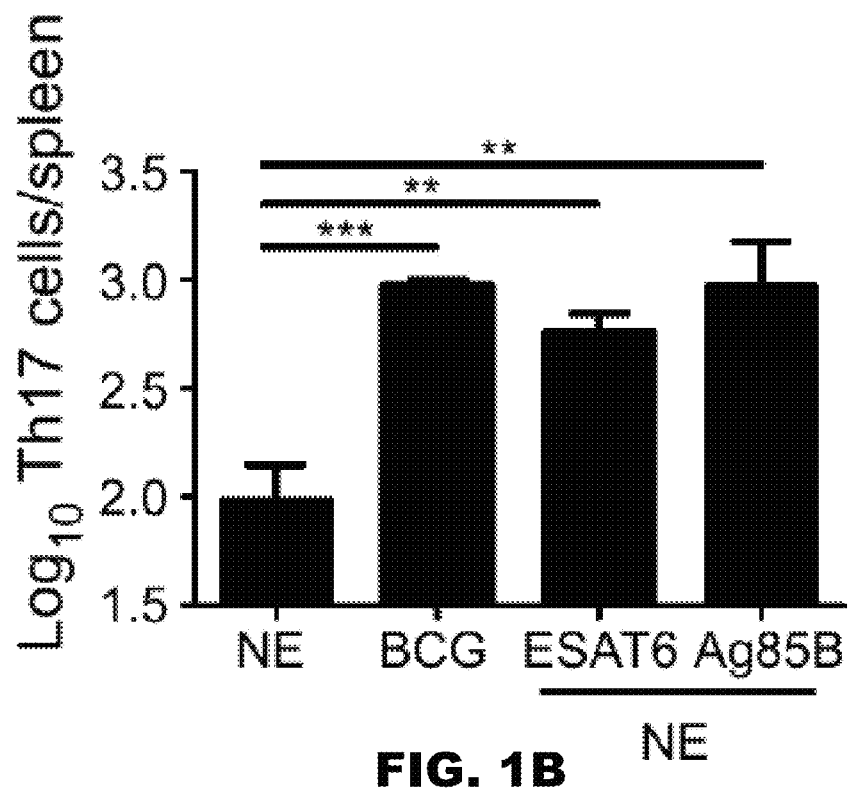
Figure 1C:
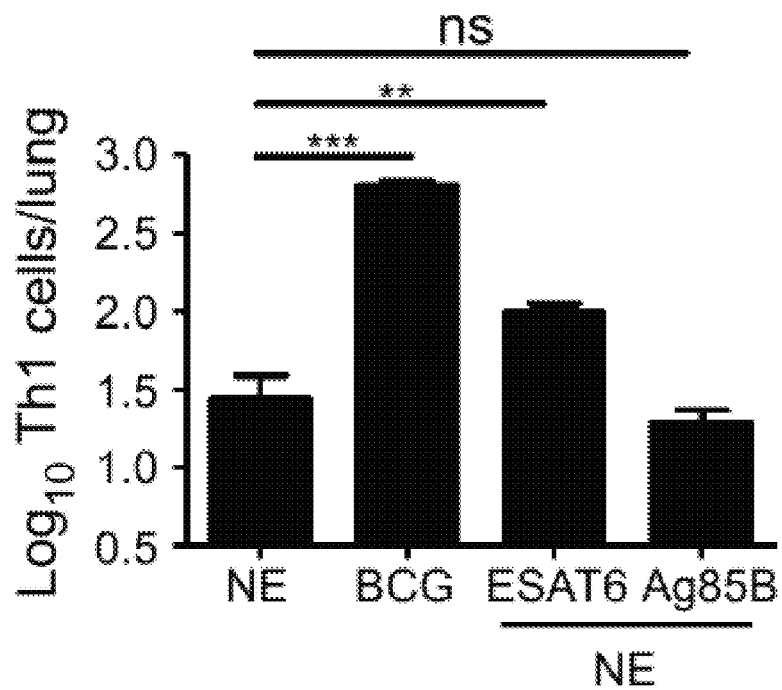
Figure 1D:
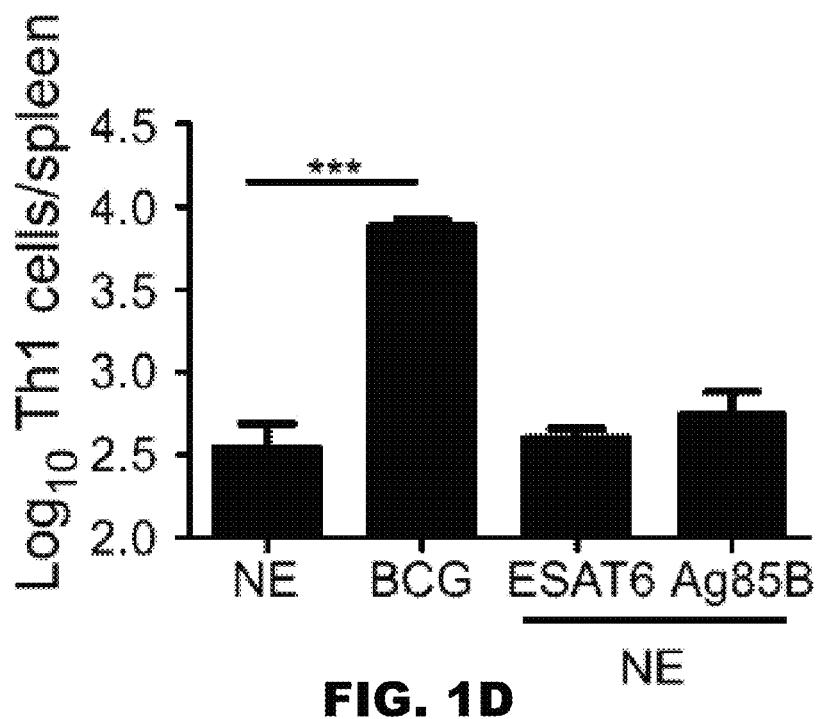

Mucosal vaccines induce better mucosal immunity and confer superior protection against mucosal infectious diseases, including TB,[12-15] when compared to systemic routes of immunization.[16] Importantly, we and others have recently demonstrated that mucosal vaccination of Mtb antigens (Ag) in Heat Labile enterotoxin (HLT)[8] or cholera toxin[17] induced mucosal Th17 responses, which confer protection upon Mtb challenge. Our mechanistic studies demonstrated that IL-17 induced chemokines localize cytokine-producing T cells near Mtb-infected macrophages, forming lymphoid follicles within granulomas to mediate Mtb control.[11, 18] In combination with DC transfer, a HLT-TB mucosal vaccine can provide superior near-sterilizing vaccine-induced protection against Mtb infection.[8, 17, 19] Despite the ability of these experimental mucosal adjuvants to induce protective Th17 responses and confer vaccine-induced protection, there are serious concerns regarding the safety of toxin subunits as mucosal adjuvants in human vaccines. For example, Bell's palsy has been observed following intranasal (I.N.) application of the vaccine Nasalflu, which contains *Escherichia coli* HLTs as an adjuvant.[20] Therefore, there is an urgent need to identify safe and effective mucosal TB vaccines that can induce lung mucosal Th17 responses for use in humans.

Nanoemulsions (NE) are oil-in-water emulsions formulated with an antigen. NE adjuvant was safe and well-tolerated in human volunteers when used as a flu vaccine, and elicited both systemic and mucosal immunity following a single intranasal vaccination.[21] When delivered with antigen in mice by intranasal route, the NE-based vaccine induces Th17 responses.[22] In the current study, we tested whether NE-adjuvanted TB vaccine will confer protection against Mtb infection, and provide any advantage when compared to use of BCG vaccination. Our results show that mucosal delivery of NE along with Mtb immunodominant antigens (NE-TB vaccine) can confer Mtb control, to levels similar to BCG vaccination in mice.

Example 1. NE-TB Vaccine Induces Th17 Mucosal Responses in Mice

Mucosal vaccines induce better mucosal immunity and confer superior protection against TB, when compared to systemic routes of immunization. Furthermore, mucosal route of vaccination induces Th17 responses in mice.[8] It was determined whether intranasal delivery of NE along with Mtb immunodominant antigens could drive mucosal Th17 and/or Th1 responses in vaccinated mice. B6 mice were mucosally vaccinated and boosted twice with NE adjuvant formulated with either immunodominant Mtb antigen ESAT6 or Ag85B whole protein. Two weeks after the last booster vaccination, we determined antigen-specific IFNγ and IL-17 CD4+ T cell responses in lungs and spleens of vaccinated mice. Our results show that mucosally vaccinated mice induced Th17 mucosal responses in the lung, while neither BCG vaccination nor mucosal delivery of NE by itself induced any Mtb-specific Th17 lung responses (FIG. 1A). Both BCG vaccination and mucosal delivery of NE with Mtb Ag induced Th17 responses in the spleen (FIG. 1B). BCG vaccination induced Th1 responses in both lung and the spleen. However, while ESAT-6 in NE adjuvant induced some Th1 responses in the spleen, Ag85B along with NE did not potently induce Th1 responses in either lung or spleen (FIG. 1C and FIG. 1D). Thus, data show that mucosal vaccination of NE along with Mtb Ag induces both systemic and mucosal Th17 responses in the lung, while less effective at inducing Th1 responses in the lung.

Figure 2A:
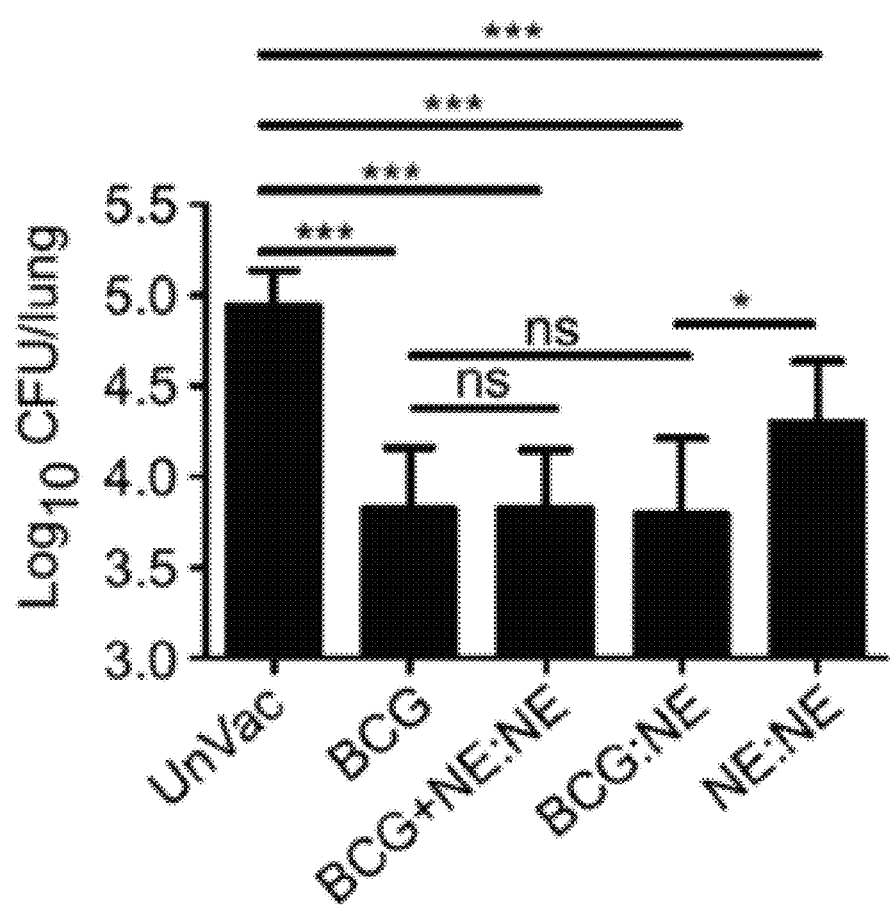
FIG. 2A and FIG. 2B depict graphs and FIG. 2C, FIG. 2D, FIG. 2E, FIG. 2F, and FIG. 2G depict histology showing NE-TB vaccination conferred vaccine-induced protection and decreased TB disease upon *Mycobacterium tuberculosis* (Mtb) challenge. Mice were either left unvaccinated (Un-Vac), vaccinated s.c. with BCG (BCG), mucosally vaccinated and boosted with Ag85B/ESAT-6 proteins with NE (NE:NE), or with BCG s.c. and boosted with NE-TB (BCG: NE) or vaccinated concurrently both BCG (S.C.) and mucosally with NE-TB, and boosted with NE-TB (BCG+ NE:NE), and rested for 4 weeks after which mice were challenged with Mtb HN878 (~100 CFU). Mtb colony forming units (CFU) in the lung (FIG. 2A) were determined on 30 days post-infection (dpi). Lung formalin-fixed paraffin-embedded (FFPE) sections from each treatment group were stained with H&E and percentage of lung inflammation was quantitated on H&E slides (FIG. 2B). Representative images of H&E stained lung FFPE sections from each treatment group are shown in FIG. 2C, FIG. 2D, FIG. 2E, FIG. 2F, and FIG. 2G.

Example 2. NE-TB Vaccination Confers Vaccine-Induced Protection and Decreases TB Disease Upon Mtb Challenge Results show that NE-adjuvanted with Mtb immunodominant antigens induces potent Th17 mucosal responses, while ESAT-6 and not Ag85B induce systemic Th1 responses. It was nest determined whether a NE-TB vaccine (NE formulated with both ESAT6/Ag85B proteins) was protective in a mouse model of Mtb challenge, and whether NE-TB vaccine delivered as a booster to BCG vaccination improved protection upon Mtb challenge. B6 mice were mucosally vaccinated with NE-TB vaccine using different protocols: mice received intranasal vaccination with NE-TB followed by two intranasal boosts 3 weeks apart; (NE:NE), or mice received a single priming dose of BCG s.c. followed sequentially by two intranasal NE boosts; (BCG:NE), or mice received s.c. with BCG concurrently with simultaneous intranasal NE-TB as the priming immunization, followed by two intranasal NE-TB boosts alone, without BCG (BCG+ NE:NE). Additionally, we included mice that received BCG vaccination S.C. alone (BCG). Mice receiving PBS were included as unvaccinated controls. All groups of mice were rested for four weeks, and then challenged with a low dose of aerosolized hypervirulent clinical strain, Mtb HN878. BCG vaccination resulted in significant protective efficacy upon Mtb challenge (FIG. 2A). NE-TB vaccine also resulted in significant protection when compared to Mtb CFU in unvaccinated Mtb challenged mice (FIG. 2A). Additionally, mucosal delivery of NE-TB vaccine either concurrently at the time of BCG vaccination or alone as a booster to initial BCG vaccination did not alter Mtb control in vaccinated mice (FIG. 2A). These results suggest that NE-TB mucosal vaccine is protective upon Mtb challenge and provides protection, similar to the gold standard vaccine, BCG.

Figure 2B:
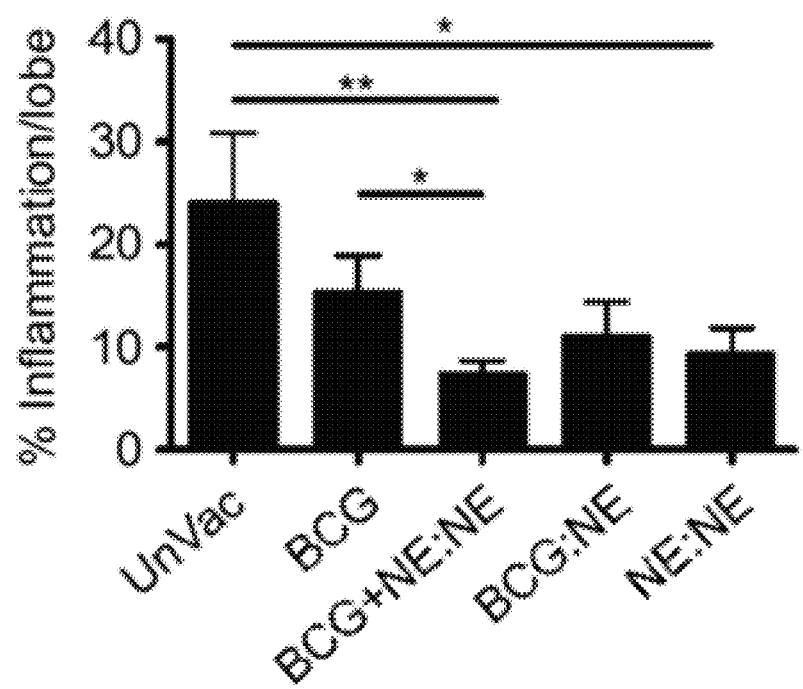
Figure 2C:
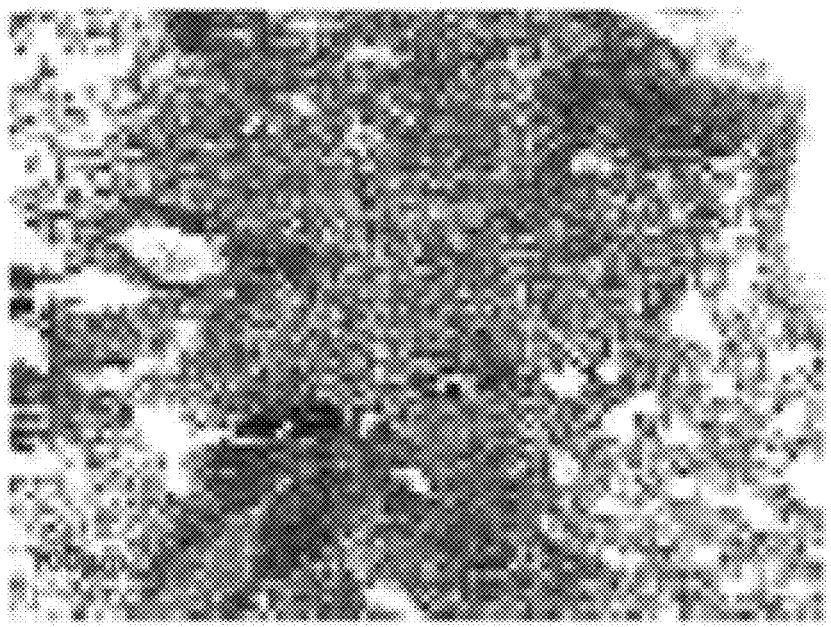
Figure 2D:
Figure 2E:
Figure 2F:
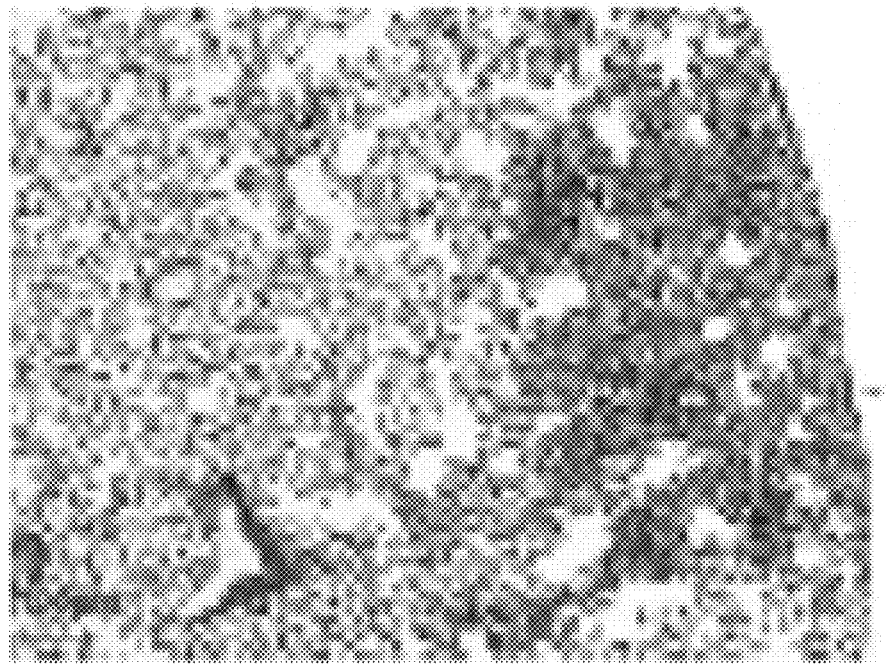
Figure 2G:
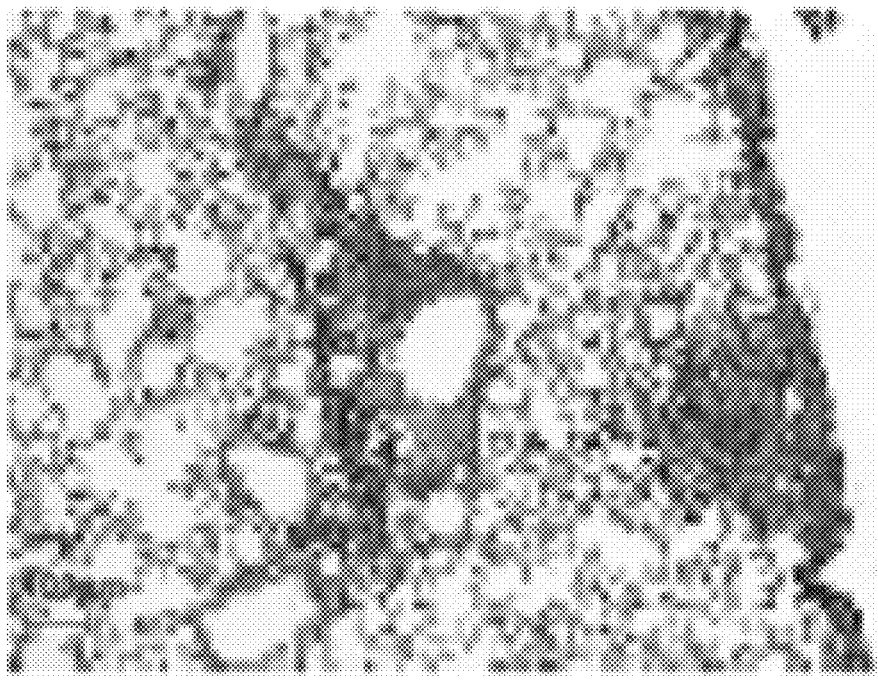

Although prevention of infection and Mtb control are readouts of vaccine efficacy, alleviation of TB disease is another critical outcome for an effective vaccine response. Thus, lung inflammation was measured in the different groups of vaccinated Mtb-infected mice. It was found that while unvaccinated Mtb-infected mice demonstrated increased inflammation, BCG vaccination moderately dampened lung inflammation in Mtb-infected mice (FIG. 2B and FIG. 2D) compared to unvaccinated mice (FIG. 2C). Interestingly, NE-TB vaccination either by itself (NE:NE; FIG. 2G) or when carried out sequentially after a priming vaccination using BCG alone (BCG:NE; FIG. 2F), or when administered concurrently with BCG vaccination for the priming dose (BCG+NE:NE; FIG. 2E) resulted in further and improved dampening of lung inflammation, when compared to unvaccinated Mtb-infected mice, or animals vaccinated using BCG alone (FIG. 2B and FIG. 2D). These results suggest that mucosal vaccine with NE-TB vaccine limits disease inflammation and improves disease outcome in Mtb-infected mice, even over levels conferred by the gold standard vaccine, BCG.

Figure 3A:
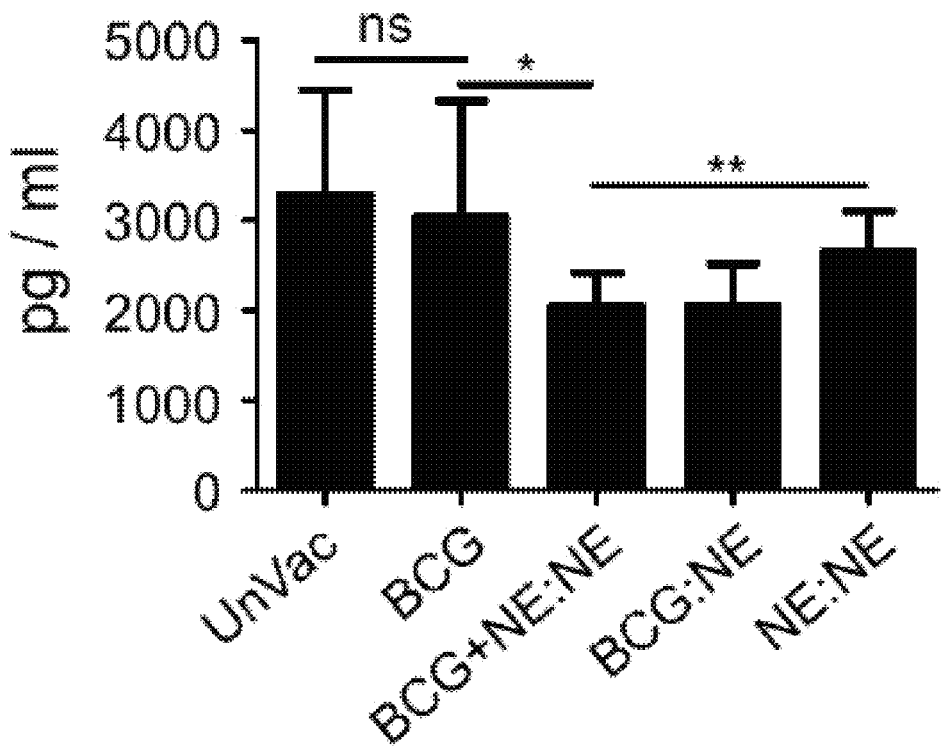
FIG. 3A, FIG. 3B, FIG. 3C, and FIG. 3D depict graphs showing decreased chemokine induction and improved B cell lymphoid follicle formation is associated with mucosal delivery of NE-TB vaccine in previously BCG vaccinated mice. Lung homogenates from vaccinated groups were used to measure chemokine levels by Milliplex assay (FIG. 3A, FIG. 3B, and FIG. 3C). Lung FFPE sections were stained for B cells and average size of B cell follicles was quantitated by immunofluorescence (IF) (FIG. 3D).
Figure 3B:
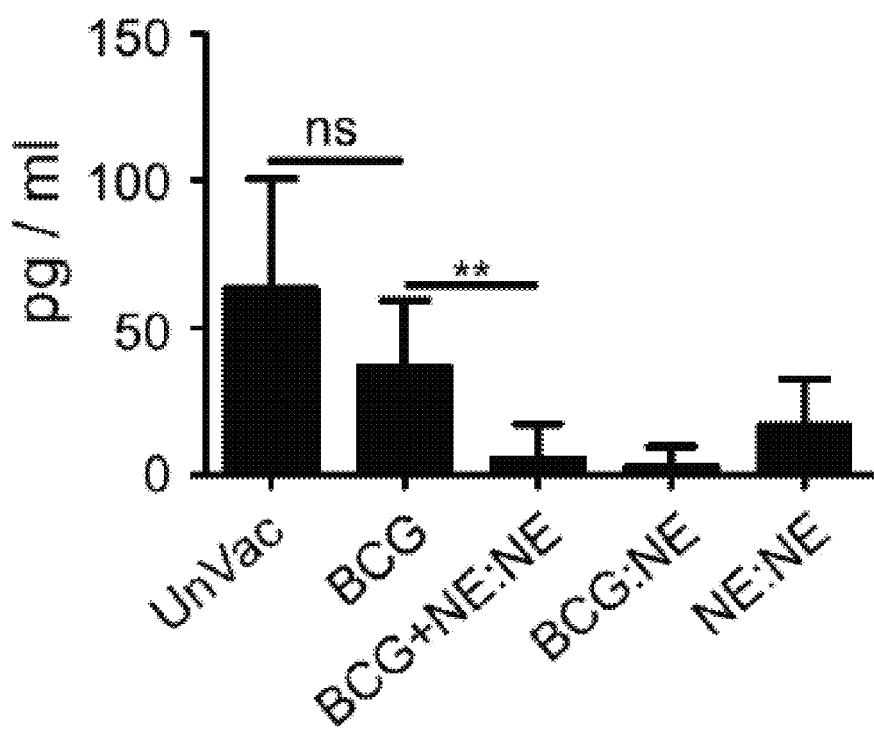
Figure 3C:
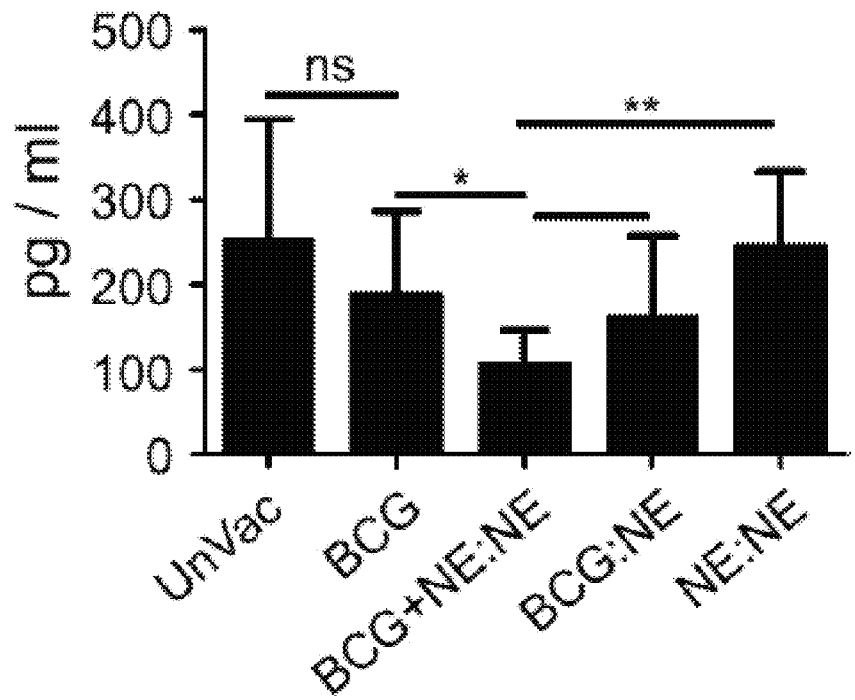
Figure 3D:
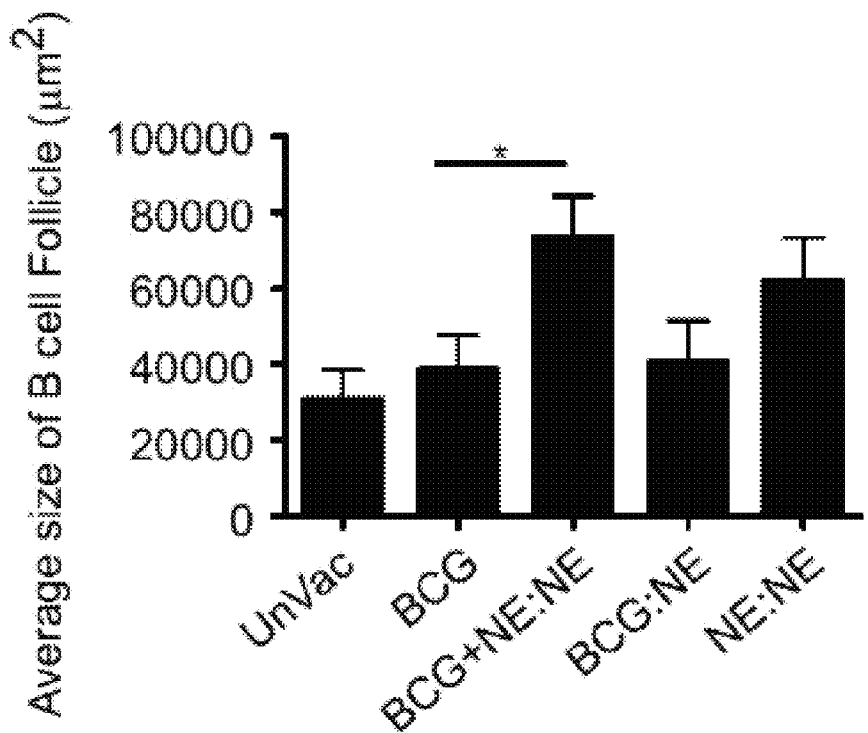

Example 3. Decreased Chemokine Induction and Improved B Cell Lymphoid Follicle Formation is Associated with Mucosal Delivery of NE-TB Vaccine in Previously BCG Vaccinated Mice Data show that a novel mucosal NE-TB vaccine confers protection and limits TB disease in Mtb-infected mice. Studies have described the generation of B cell follicle containing TB granulomas that allow for colocalization of T cells near Mtb-infected macrophages for control of Mtb infection. Thus, the area occupied by B cell follicles within TB granulomas was measured in the various groups of vaccinated and unvaccinated Mtb-infected mice. While, NE-TB vaccination resulted in formation of well-formed B cell follicle formation within TB granulomas (FIG. 3D), mice that received BCG vaccination along with concurrent mucosal NE-TB vaccine delivery resulted in most effective formation of B cell follicles within TB granulomas. Additionally, mice that received BCG vaccination along with mucosal NE-TB vaccine delivery also exhibited decreased induction of inflammatory chemokines including CXCL-9, CXCL-2 and CCL-5 (FIG. 3A, FIG. 3B, and FIG. 3C). Thus, these results together demonstrate that not only does NE-TB vaccine induce effective Mtb control, but NE-TB vaccination alone, or given alongside BCG vaccination results in decreased TB disease and induction of protective granulomas in the lung.

Discussion for Examples 1-3

TB is a significant cause of global mortality and morbidity. However as the specter of TB looms on, an efficacious human vaccine is still unavailable. Despite the urgent need for the development of an effective human TB vaccine, BCG remains the only licensed vaccine against TB for over a hundred years. Since the natural route of TB infection is through the mucosal surface, vaccines delivered through the mucosal route are known provide superior protection against Mtb infection.[14, 15] However, there is no mucosal TB vaccine that is currently in clinical trials. Thus, in this study we demonstrate that NE adjuvant already tested to be safe in humans,[22] when delivered with Mtb immunodominant antigens induces potent mucosal Th17 responses and confers protective vaccine-induced immunity in the lung. Importantly, this NE-based mucosal TB vaccine when used with BCG vaccination significantly limits TB disease severity, when compared to use of the BCG vaccination alone. Thus, our studies project the future use of NE-TB vaccine as a first-of-kind mucosal vaccine for development into a human TB vaccine.

Substantial recent evidence supports the role for Th17 cells in vaccine-mediated immunity against TB[8, 10, 17] Several mucosally delivered adjuvants such as cholera toxin,[25, 26] heat labile enterotoxins,[8] Monophosphoryl lipid A (MPL) along with chitosan,[27] when delivered with Mtb antigens in experimental models have all shown to induce potent lung Th17 responses and confer Mtb control. However, there are serious concerns regarding the safety of toxin subunits as mucosal adjuvants in human vaccines, and so far MPL and chitosan have been proven safe for human mucosal immunization.[28-30] NE-based vaccines have been tested safe for human mucosal use,[21] and thus stand out in being compatible for use in a human TB vaccine. With regard to choice of antigens, we combined the use of immunodominant antigens ESAT-6 and Ag85B, as both antigens when individually delivered in NE, induced potent Th17 responses in the lung. This is consistent with the known role for NE in activating mucosal DCs to induce IL-6, and in driving mucosal Th17 responses.[22] However, NE delivered with ESAT-6 antigen additionally induced Th1 responses in the spleen. This is surprising considering ESAT-6 protein has been shown to induce TGF-β and IL-6 in TLR-2, Myd88-dependent manner and induce Th17 responses.[31] Nonetheless, we combined use of Ag85B and ESAT-6 along with NE to drive both mucosal Th17 responses and systemic Th1 responses, for testing protective efficacy in Mtb-infected mice. Our results demonstrating that use of NE-TB vaccine in mice confers protection upon Mtb challenge further support the development of Th17-inducing vaccines for TB. However, our results here as well as published studies [8] demonstrate that while sub-unit vaccines delivered mucosally confer Mtb control, the level of protection induced by sub-unit vaccines is less when compared to protection induced by use of a live attenuated TB vaccine, such as BCG.

A hallmark of pulmonary TB in both humans and experimental animals is the formation of granulomas containing Mtb-infected macrophages.[32] Protective TB granulomas comprise of organized lymphoid structures mediated by the expression of CXCL13[33-36], which controls the formation of B cell follicles, T cell placement and the optimal activation of macrophages for Mtb control.[33-35] Our results show that use of NE-TB vaccine either by itself, or in combination with BCG reduces overall lung inflammation. Coincident with decreased TB disease, our results also demonstrate that use of NE-TB vaccine either by itself or in combination with BCG vaccination, induces effective formation of B cell follicles in the lungs of the Mtb-infected mice. It is possible that mucosal Th17 cell responses induced by NE-TB vaccines in BCG vaccinated mice drives rapid lung CXCL-13 expression to induce early lymphoid structures, thus decreasing TB disease, expression of inflammatory chemokines, and mediating Mtb control. Therefore the use of NE-TB vaccine may be effective in not only providing protection against Mtb challenge but will also aid in lowering the level of inflammation in the lungs, and perhaps even limit TB reactivation in latently infected individuals. The current slate of TB vaccines are projected to replace BCG with an improved live vector-based vaccine, or as a boost in BCG primed hosts.[1] Thus, our data demonstrating that co-administration of the NE-TB mucosal vaccine along with BCG vaccination significantly decreases TB disease, could be pave way to a strategy to improve the efficacy of BCG vaccination in humans. Further validation of the NE-TB vaccine in NHP model is necessary to test the efficacy of this vaccine candidate for use in humans in protecting against Mtb infection.

Methods for Examples 1-3

Mice:

C57BL/6J, (Jackson Laboratories, Bar Harbor, Me.) mice were bred under specific pathogen-free conditions at the Washington University in St. Louis. Mice maintained were used at 6 to 8 weeks of age and sex matched for all experiments. All animal experiments were performed in accordance with National and Institutional guidelines for animal care under approved protocols.

Vaccination and Mtb Infection:

Control mice were vaccinated with 1×106 colony forming units (CFU) BCG subcutaneously (s.c.) as relevant controls.[23] The antigen proteins, ESAT-6 and Ag85B, were purchased from BEI resources (BEI Resources, Manassas, Va.). For intranasal vaccinations, vaccine formulation comprised of a suspension of 20% NE ($W_{80}5$ EC, See Table 1 for formulation) and ESAT-6, Ag85B proteins was delivered by the intranasal route. The intranasal immunizations were carried out using a sterile pipette tip applied to the nares, and the mice were administered 12 μl (6 μl/nare) of the NE formulation containing 25 μg of antigen mixed with 20% NE. The NE-TB vaccine thus prepared was delivered to 6-8-week-old C57BL/6, mice three times at three week intervals, while mock-immunized mice received PBS as control. Four weeks after the last booster immunization, mice were challenged by aerosol with Mtb strain HN878 (BEI Resources, Manassas, Va.). *Mycobacterium bovis* Bacille Calmette Guerin (BCG Pasteur, Source: Trudeau Institute) and *Mycobacterium tuberculosis* strain HN878 (BEI Resources, Manassas, Va.) were grown to mid-log phase in Proskauer Beck medium containing 0.05% TWEEN 80 and frozen in 1 mL aliquots at −80° C. Four weeks after challenge, unvaccinated and vaccinated mice were sacrificed by $CO_2$ asphyxiation, and the lungs were aseptically excised and individually homogenized in physiological saline solution. Serial dilutions of lung homogenates were plated on 7H11 agar for CFU and counted after 3 weeks of incubation at 37° C. as described before [24].

TABLE 1

| $W_{80}5EC$ Formulation (Droplet size ~400 nm) | |
|---|---|
| Aqueous Diluent | Purified Water |
| Hydrophobic Oil (Core) | Soybean Oil |
| Organic Solvent | Dehydrated alcohol (anhydrous ethanol) |
| Surfactant | Polysorbate 80 |
| Antiseptic | Cetylpyridinium chloride |

ELISApot Assay:

Antigen-specific IFNγ- and IL-17-producing cells in immunized lungs were detected by ELISpot assay as described [23]. Briefly, 2 weeks after the last immunization, lung single cell suspension from immunized mice were seeded in antibody-coated plates at an initial density of 5×105 per well. Irradiated syngeneic spleen cells (2000 RADS), IL-2 (final concentration of 10 U/mL) in the presence of ESAT-6 or Ag85B proteins (10 μg/mL) were added to the cultures. After 18 hours, the cells secreting IFNγ or IL-17 were detected using BCIP/NBT (Sigma, St. Louis, Mo.) according to the manufacturer's instructions. The frequency of responding cells was calculated using IMMUNOSPOT software and total number of cytokine-producing cells were determined (Cellular Technology Limited, Shaker Heights, Ohio).

Evaluation of Inflammatory Lesions and Formation of B Cell Follicles in Vaccinated Mice by Bright Field and Fluorescent Microscopy:

Lungs from vaccinated and unvaccinated Mtb-infected mice were perfused with 10% neutral buffered formalin and embedded in paraffin. 5 μm paraffin lung sections were stained with hematoxylin and eosin, and percentage of area occupied by inflammatory cell infiltrates was calculated with an automated tool of the ZEISS AXIOPLAN microscope. Serial sections of 5 μm paraffin embedded lung tissues were also stained with primary antibodies specific for CD3 (Clone M-20, Santa Cruz Biotechnology) and biotinylated antibodies against CD45R/B220 (clone RA3-6B2, BD Biosciences). To visualize the B cell follicles and T cells inside TB granulomas, lung sections were incubated with ALEXA FLUOR 568 donkey anti-goat IgG (A11057, Life technologies) and ALEXA FLUOR 488 streptavidin (S11223, Life technologies). After washing slides, they were mounted with prolong gold antifade with DAPI (P36931, Life technologies) and representative pictures were taken with a AXIOPLAN ZEISS microscope and recorded with a Hamamatsu camera. Morphometric analysis of B cell follicles was performed with the outline automated tool of the ZEISS AXIOPLAN microscope.

Detection of Cytokines in Culture Supernatants:

Culture supernatants were assayed for multiple cytokines either using MILLIPLEX (EMD Millipore, Billerica, Mass.) or for single cytokine proteins using DUOSET ELISA (R&D Systems, Minneapolis, Minn.), according to recommended standard protocols.

Statistical Analysis:

Statistical analyses were performed using GRAPHPAD PRISM (La Jolla, Calif., USA). For experiments with two groups, two-tailed student t-tests were performed. For two or more groups, a one-way ANOVA was used.

Introduction for Examples 4-6

Tuberculosis (TB) caused by *Mycobacterium tuberculosis* (Mtb) is a leading cause of death worldwide, with an estimated nine million new cases of TB diagnosed each year, resulting in 1.4 million deaths annually [43]. Although BCG vaccination is effective against childhood forms of TB [44], and in decreasing childhood TB morbidity [44], it provides variable efficacy against adult pulmonary TB. Thus, over the past two decades, concerted efforts have been made to develop new vaccines for TB that will provide improved protection upon Mtb exposure. Modern candidate TB vaccines have focused on induction of T cells responses, primarily CD4+ T cells producing interferon gamma (IFN-γ) [45] and interleukin 17A (IL-17A)[46]-[49]. Despite these efforts, most TB vaccines reduce the burden of lung Mtb by −0.5 to 1.0 log in animal challenge models [45][50]-[52]. Recombinant live mycobacterial vaccines confer improved protection (~2 log reduction) when compared to subunit and virally-vectored TB vaccines. Examples of recombinant vaccines include the recombinant *Mycobacterium smegmatis* vaccine, which induces sterilizing immunity in the liver, but not the lung [53]; recombinant BCG over-expressing *Listeria monocytogenes* listeriolysin and lacking Urease C [52],[54]; and the recombinant Mtb vaccine lacking phoP [55] and mosR [56]. Other work has highlighted the benefit of administering recombinant Mtb vaccines mucosally, showing that macaques vaccinated with the attenuated Mtb mutant lacking SigH had sterile protection in some TB lesions [57]. Despite these promising studies, most TB vaccines under development only suppress Mtb infection, without controlling Mtb growth to induce sterilizing vaccine-immunity in animal models. Mtb prevents antigen presentation by APCs, resulting in delayed T cell responses following primary Mtb infection. This delay in accumulation of activated T cells provides an early period of time during which Mtb can replicate unrestricted and establish infection in the lung. Our new data show that the lack of sterilizing vaccine-induced immunity to TB vaccines is not due to poor induction or function of vaccine-induced CD4+ T cells, but due to delayed activation and accumulation of recall CD4+ T cell responses in the lung following Mtb infection. Using novel strategies, we show that this T cell bottleneck can be overcome by delivery of activated Mtb antigen (Ag)-pulsed dendritic cells (DCs) into the lungs of BCG vaccinated Mtb-infected mice.

Figure 4A:
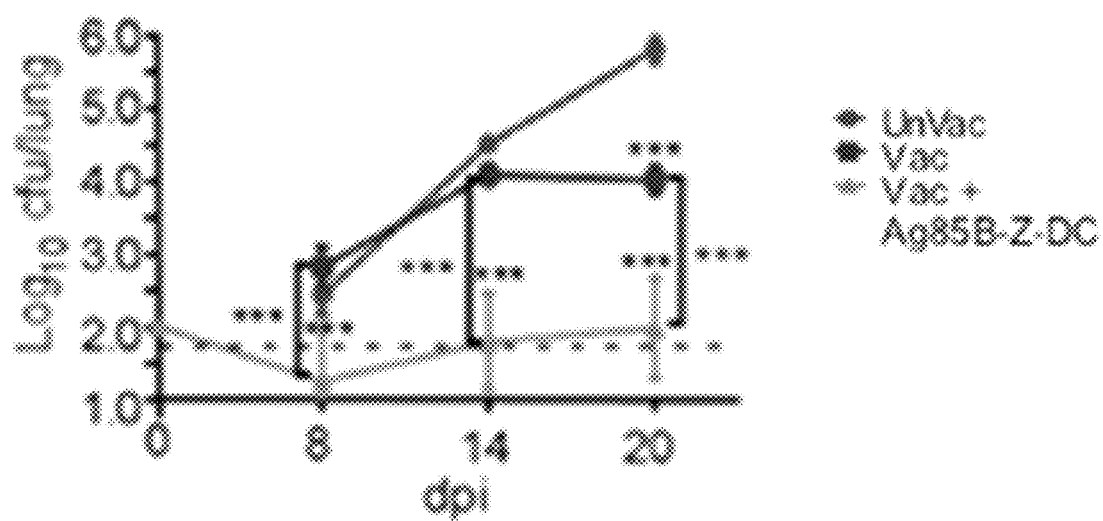
FIG. 4A, FIG. 4B, FIG. 4C, FIG. 4D, FIG. 4E, and FIG. 4F show dendritic cell (DC) transfer induces sterilizing vaccine-immunity. B6 mice were vaccinated with BCG s.c. followed by mucosal boost with $Ag85B_{240-254}$ peptide (Ag85B) in mucosal adjuvant, rested for 4 weeks and infected with Mtb HN878 (~100 CFU). Vaccinated mice received Ag85B-treated DCs on −1 and 4 dpi.
Figure 4B:
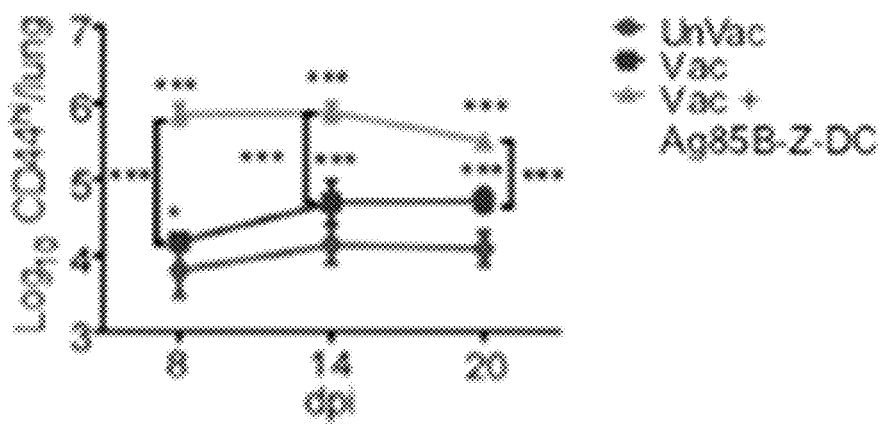
Figure 4C:
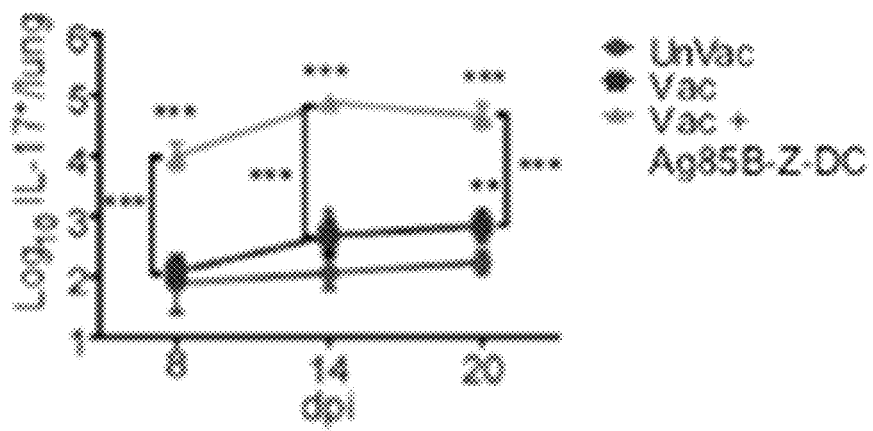
Figure 4D:
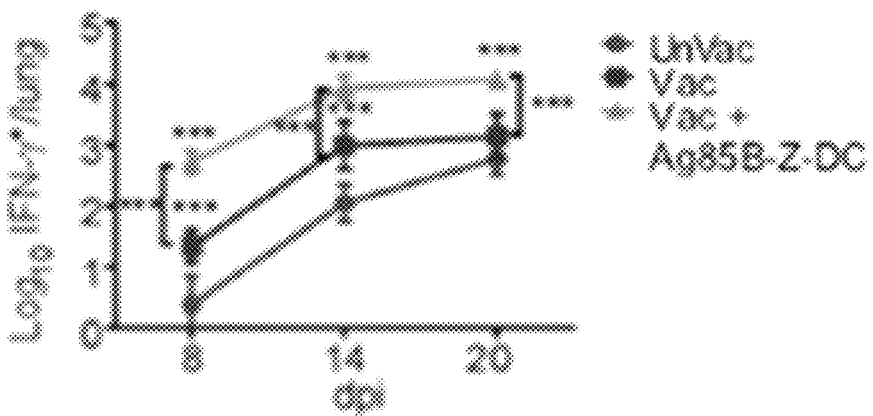
Figure 4E:
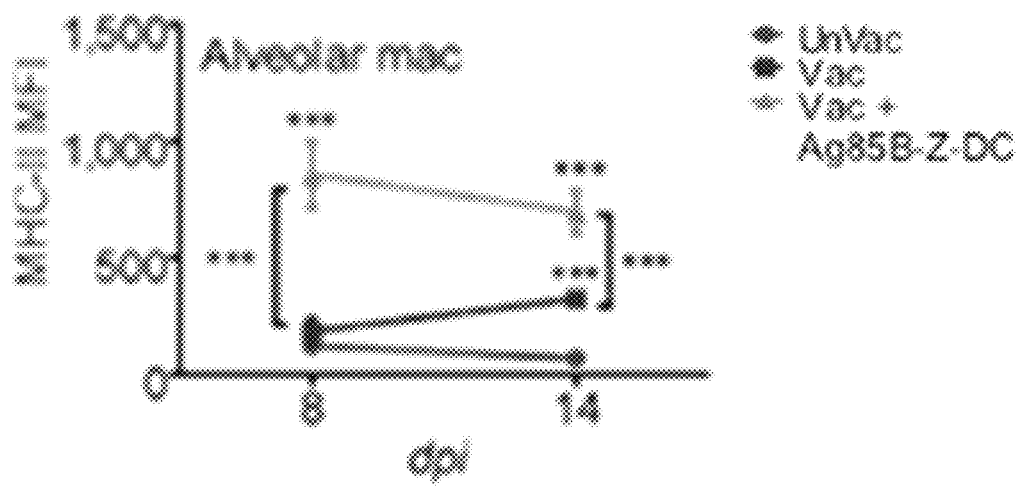
Figure 4F:
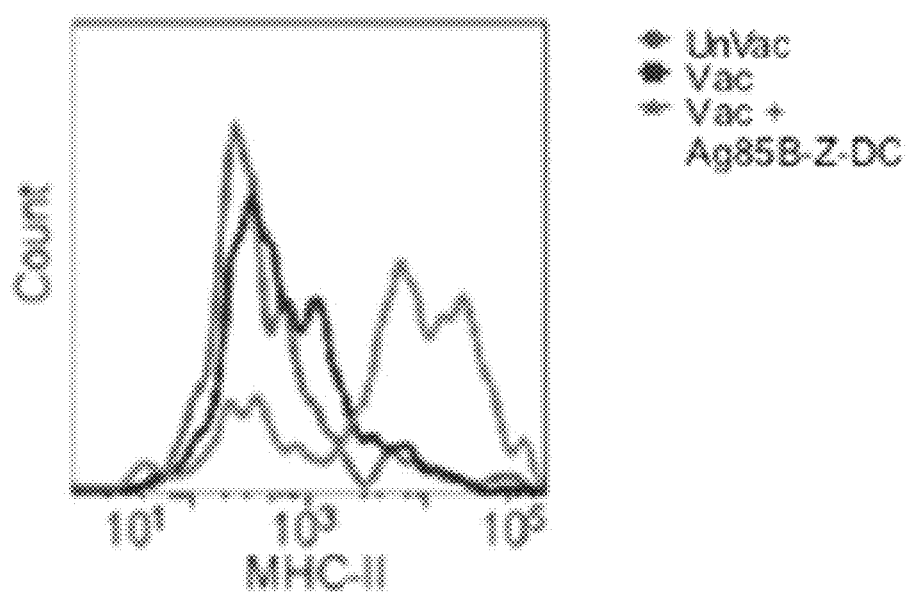

Example 4. Administration of Activated-Primed DCs Accelerates the Timing of T Cell Accumulation in the Lungs and Leads to Sterilizing Vaccine-Induced Immunity in Mtb-Infected Vaccinated Mice First assessed was whether a delay in accumulation of CD4+ T-cell recall responses was due to an inherent deficiency in the ability of the vaccine-induced T cells to respond to antigen exposure. C57BL/6 (B6) mice, which were vaccinated subcutaneously (s.c.) with BCG, rested for 4 weeks followed by a mucosal boost with $Ag85B_{240-254}$ peptide. Following a period of rest for 4 weeks, vaccinated mice were infected with Mtb (Vac). Other vaccinated mice received activated-primed DCs, wherein the DCs with pulsed with the $Ag85B_{240-254}$ peptide and activated with zymosan one day before infection with Mtb and again 4 days after infection with Mtb (Vac+Ag85B-Z-DC). Ag85B-Z-DC administration substantially delays bacterial burden in the lungs up to 21 dpi compared to unvaccinated mice and vaccinated mice that did not receive Ag85B-Z-DC (FIG. 4A). Lungs harvested from the experimental groups, subjected to flow cytometry demonstrated that Ag85B-Z-DC administration increased $CD44^{hi}$ (FIG. 4B), IL-17 (FIG. 4C), and IFN-γ (FIG. 4D) amounts in the lung compared to unvaccinated mice and vaccinated mice that did not receive Ag85B-Z-DC. Flow cytometry (FIG. 4F) and immunofluorescence (FIG. 4E) revealed that lung alveolar macrophages were elevated in the vaccinated mice receiving Ag85B-Z-DCs compared to unvaccinated mice and vaccinated mice that did not receive Ag85B-Z-DC. The data suggest that administration of activated-primed DCs substantially accelerates the timing of CD4+ T cell accumulation in the lungs, early and rapid activation of macrophages, and leads to sterilizing vaccine-induced immunity in Mtb-infected BCG vaccinated mice.

Example 5. Administration of Activated-Primed DCs Induces Early Genes Associated with Antigen-Presenting Cell Activation Using RNASeq analysis, we have generated a gene signature in BCG vaccinated mice receiving DC administration that is associated with the superior vaccine immunity induced upon Mtb infection. This gene signature reflects upregulation of pathways associated with rapid an effective activation of lung DCs and T cell pathways. Several genes involved in early T-cell activation, macrophage function, as well as chemokines involved in B-cell follicle formation, were significantly upregulated. Specifically, we found genes associated with activation of CD103+DC and CD40 pathways upregulated in DC transfer-recipient vaccinated Mtb-infected mice exhibiting superior Mtb control (data not shown).

Figure 5:
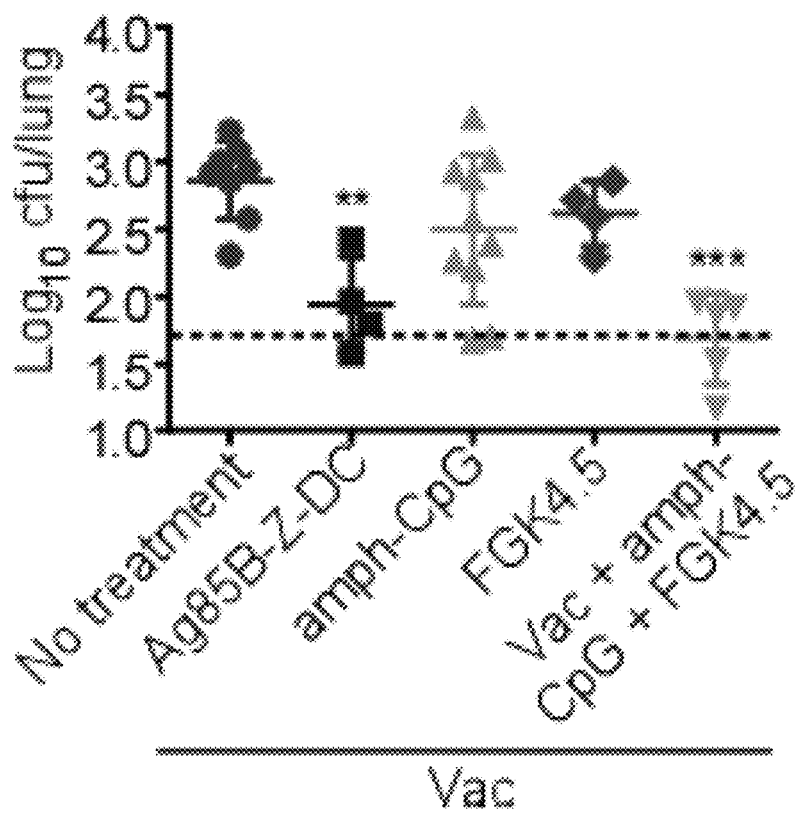
FIG. 5 depicts Amph-CpG and CD40-agonist administration improved Mtb control in vaccinated hosts. Mice were vaccinated with BCG s.c. and rested for 4 weeks. Vaccinated mice were infected with Mtb HN878 and treated with either Ag85B-Z-DC, amph-CpG alone (1.24 nmol), FGK4.5 alone (100 μg), or both amph-CpG and FGK4.5 along with Ag85B (5 μg) on −1 and 4 dpi. Mice were harvested at 8 dpi. Lung bacterial burden was determined by plating. *p≤0.05, p≤0.01, *p≤0.001 by student's t-test.

Example 6. The CD103+ DC and CD40 Pathway can be Targeted for Improved Mtb Control in Vaccinated Mice To target the CD103+DC and CD40 pathways, we assessed if activation of the CD40 pathway and targeting endogenous CD103+ mucosal DCs in standard BCG-vaccinated Mtb-infected mice, can mimic the effects of DC transfer and induce superior Mtb control. Systemic administration of amphiphilic-CpG (amph-CpG) in mice is taken up by DCs and macrophages, and enhances T-cell responses to peptide vaccines. Further, exvivo treatment of DCs with amph-CpG upregulates CD103 expression. FGK4.5 is an agonistic CD40 antibody that has been shown to activate DCs. BCG-vaccinated Mtb-infected mice received either Ag85B-Z-DCs, amph-CpG along with FGK4.5, or either amph-CpG or FGK4.5 alone, at −1 and 4 dpi and Mtb burden in the lungs was assessed at 8 dpi (FIG. 5). While delivery of either amph-CpG alone or FGK4.5 alone did not induce significant vaccine protection, data show that delivery of amph-CpG and FGK4.5 together in vaccinated mice results in early Mtb control, similar to that seen in vaccinated Mtb-infected hosts receiving Ag85B-Z-DC.

Discussion for Examples 4-6

Results have thus determined delayed T cell vaccine responses as a key bottleneck for the failure of BCG vaccine to induce sterilizing protection against Mtb infection. If targeting DCs can induce sterilizing vaccine-immunity across different classes of TB vaccines, it can be concluded that the T cell bottleneck is a universal bottleneck that can be targeted to improve vaccine efficacy across all classes of TB vaccines. In contrast, if we find that targeting DCs only induces sterilizing vaccine-immunity across a specific class of TB vaccines, it can be concluded that bottlenecks are specific to the type of immune responses induced by the class of TB vaccines, and not universal. Regardless, fully understanding the immune bottlenecks that impact TB vaccine efficacy as described herein can provide a roadmap for the type of early immune responses that a sterilizing TB vaccine should induce.

Methods for Examples 4-6

Mice:

C57BL/6J, (Jackson Laboratories, Bar Harbor, Me.) mice were bred under specific pathogen-free conditions at the Washington University in St. Louis. Mice maintained were used at 6 to 8 weeks of age and sex matched for all experiments. All animal experiments were performed in accordance with National and Institutional guidelines for animal care under approved protocols.

Bacterial Infection and Vaccination:

*Mycobacterium bovis* Bacille Calmette-Guerin (BCG Pasteur, Source: Trudeau institute), Mtb strain HN878 (Source: BEI Resources) and Mtb strain H37Rv (Source: Trudeau Institute) were grown to mid-log phase in Proskauer Beck medium containing 0.05% Tween80 and frozen in 1 ml aliquots at −80° C.

Mice were vaccinated with $1\times10^6$ c.f.u. BCG s.c. and 4 weeks later received 133 µg $Ag85B_{240-254}$ peptide (New England Peptide, Gardner, Mass., USA) along with 1 µg heat-labile enterotoxin (LT-IIb) intranasally in 20 µl (10 µl per nare). In some experiments, mice only received mucosal vaccination with three doses, 2 weeks apart of 133 µg $Ag85B_{240-254}$ peptide in 1 µg LT-IIb intranasally. In other experiments, mice only received $1\times10^6$ c.f.u. BCG s.c. as a model of parenteral vaccination. Four or 10 weeks after the final vaccination, mice were infected with 100 c.f.u. (low dose) or 1,000 c.f.u. (high dose) Mtb HN878 via aerosol using a Glas-Col aerosol exposure system (Glas-Col, Terre Haute, Ind., USA). At given time points following infection, organs were collected, homogenized and tissue homogenates plated in serial dilutions on 7H11 agar (BD Biosciences, San Jose, Calif., USA) to assess bacterial burden.

In Vitro Culture of DCs and Macrophages:

Bone marrow-derived DCs (BMDCs) and bone marrow-derived macrophages (BMDMs) were generated from B6 mice. Cells were isolated from the femur and tibia, and cultured at $1\times10^6$ cells $ml^{-1}$ in 10 ml complete DMEM (cDMEM) supplemented with 20 ng $ml^{-1}$ recombinant mouse GM-CSF (Peprotech, Rocky Hill, N.J., USA) for 3 days at 37° C. in 7.5% $CO_2$, at which point, an additional 10 ml cDMEM supplemented with 20 ng $ml^{-1}$ recombinant mouse GM-CSF was added. Non-adherent cells (BMDCs) were collected on the seventh day of culture, and counted and plated at $2\times10^6$ cells $ml^{-1}$ in cDMEM. Adherent BMDMs were collected at the same time by scraping and cultured at $1\times10^6$ cells $ml^{-1}$. For BMDC stimulation, Ag85B240-254 peptide (20 µg $ml^{-1}$) and Zymosan (Invitrogen, San Diego, Calif.) was added at 25 µg $ml^{-1}$. Cells were stimulated for 16 h before being collected, washed, counted, and instilled i.t. into mice at $1\times10^6$ cells in 50 µl on the day before infection and 4 dpi. Supernatants from stimulated in vitro cultures were collected and frozen at −80° C. for analysis by enzyme-linked immunosorbent assay and multiplex assay. In some experiments, BMDCs were treated with 1.24 nmol amph-CpG.

Amph-CpG and FGK4.5 Treatment of Mice:

Amph-CpG was prepared as follows. Briefly, solid phase DNA synthesis and 5' lipophilic conjugation were carried out using an ABI 394 synthesizer. The sequence used was murine oligodeoxynucleotides (ODN) class B sequence 1,826 with two guanine spacers: 5'-diacyl lipid-*G*G*T*C*C*A*T*G*A*C*G*T*T*C*C*T*G*A*C*G*T*T-3'. Am ph-CpG was delivered to mice in 50 µl i.t. at 1.24 nmol per mouse. The CD40 agonist FGK4.5 (R&D Systems, Minneapolis, Minn., USA) was delivered in 50 µl i.t. at 100 µg per mouse. Both treatments were delivered with 5 µg Ag85B peptide.

RNA-Seq and Gene Set Enrichment Analysis:

Total RNA was isolated from lung tissue using an RNeasy RNA isolation kit (Qiagen, Valencia, Calif., USA). Each sample was assessed using Qubit 2.0 fluorometer (Invitrogen, Thermo Fisher) and Agilent Tapestation 2200 (Agilent Technologies, Santa Clara, Calif., USA). Sequencing libraries were generated using Illumina TruSeq RNA Access library prep kit (Illumina, San Diego, Calif., USA) following the manufacturer's protocol. Cluster generation and 75 bp single read single-indexed sequencing was performed on Illumina NextSeq 500 (Illumina). Sequencing analysis was done using mRNA-seq Analysis on Maverix Analytic Platform (Maverix Biomics, Inc, San Mateo, Calif.). Raw sequencing reads from Illumina sequencing platform that was converted into FASTQ file format were quality checked for potential sequencing issues and contaminants using FastQC. Adapter sequences, primers, Ns and reads with quality score <28 were trimmed using fastq-mcf of ea-utils and Trimmomatic. Reads with a remaining length of fewer than 20 bp after trimming were discarded. Single reads were mapped to the mouse genome (m10) using STAR in a strand specific manner. Cufflinks was used to determine fragments per kilobase of transcript per million mapped reads (FPKM) levels for each gene from the STAR alignment and was used as input for Cuffdiff. Pairwise differential expression was quantified using Cuffdiff. Read counts were then normalized across all samples and significant differentially expressed genes were determined by adjusted P value with a threshold of 0.05. For Gene Set Enrichment Analysis we have selected expressed genes from GSE11005 (top 10,000 based on average expression level). We then assembled ranked list using signed statistics values and performed pre-ranked GSEA using top 100 vaccine upregulated genes as a query gene set.

REFERENCES

[1] Xing Z, Jeyanathan M, Smaill F. New approaches to TB vaccination. Chest. 2014; 146:804-12.
[2] Lienhardt C, Fruth U, Greco M. The blueprint for vaccine research & development: walking the path for better TB vaccines. Tuberculosis (Edinb). 2012; 92 Suppl 1:S33-5.
[3] Rook G A, Dheda K, Zumla A. Immune responses to tuberculosis in developing countries: implications for new vaccines. Nat Rev Immunol. 2005; 5:661-7.
[4] Hawkridge T, Scriba T J, Gelderbloem S, Smit E, Tameris M, Moyo S, et al. Safety and immunogenicity of a new tuberculosis vaccine, MVA85A, in healthy adults in South Africa. J Infect Dis. 2008; 198:544-52.
[5] Tameris M, Geldenhuys H, Luabeya A K, Smit E, Hughes J E, Vermaak S, et al. The candidate TB vaccine, MVA85A, induces highly durable Th1 responses. PLoS One. 2014; 9: e87340.
[6] Tameris M D, Hatherill M, Landry B S, Scriba T J, Snowden M A, Lockhart S, et al. Safety and efficacy of MVA85A, a new tuberculosis vaccine, in infants previously vaccinated with BCG: a randomised, placebo-controlled phase 2b trial. Lancet. 2013; 381:1021-8.
[7] Ndiaye B P, Thienemann F, Ota M, Landry B S, Camara M, Dieye S, et al. Safety, immunogenicity, and efficacy of the candidate tuberculosis vaccine MVA85A in healthy adults infected with HIV-1: a randomised, placebo-controlled, phase 2 trial. Lancet Respir Med. 2015; 3:190-200.
[8] Gopal R, Rangel-Moreno J, Slight S, Lin Y, Nawar H F, Fallert Junecko B A, et al. Interleukin-17-dependent CXCL13 mediates mucosal vaccine-induced immunity against tuberculosis. Mucosal Immunol. 2013; 6:972-84.
[9] Griffiths K L, Khader S A. Novel vaccine approaches for protection against intracellular pathogens. Curr Opin Immunol. 2014; 28:58-63.
[10] Khader S A, Bell G K, Pearl J E, Fountain J J, Rangel-Moreno J, Cilley G E, et al. IL-23 and IL-17 in the establishment of protective pulmonary CD4+ T cell responses after vaccination and during *Mycobacterium tuberculosis* challenge. Nat Immunol. 2007; 8:369-77.
[11] Monin L, Griffiths K L, Slight S, Lin Y, Rangel-Moreno J, Khader S A. Immune requirements for protective Th17 recall responses to *Mycobacterium tuberculosis* challenge. Mucosal Immunol. 2015; 8:1099-109.
[12] Chen L, Wang J, Zganiacz A, Xing Z. Single intranasal mucosal *Mycobacterium bovis* BCG vaccination confers improved protection compared to subcutaneous vaccination against pulmonary tuberculosis. Infect Immun. 2004; 72:238-46.
[13] Goonetilleke N P, McShane H, Hannan C M, Anderson R J, Brookes R H, Hill A V. Enhanced immunogenicity and protective efficacy against *Mycobacterium tuberculosis* of bacille Calmette-Guerin vaccine using mucosal administration and boosting with a recombinant modified vaccinia virus Ankara. J Immunol. 2003; 171:1602-9.
[14] Santosuosso M, Zhang X, McCormick S, Wang J, Hitt M, Xing Z. Mechanisms of mucosal and parenteral tuberculosis vaccinations: adenoviral-based mucosal immunization preferentially elicits sustained accumulation of immune protective CD4 and CD8 T cells within the airway lumen. J Immunol. 2005; 174:7986-94.
[15] Wang J, Thorson L, Stokes R W, Santosuosso M, Huygen K, Zganiacz A, et al. Single mucosal, but not parenteral, immunization with recombinant adenoviral-based vaccine provides potent protection from pulmonary tuberculosis. J Immunol. 2004; 173:6357-65.
[16] Neutra M R, Kozlowski P A. Mucosal vaccines: the promise and the challenge. Nat Rev Immunol. 2006; 6:148-58.
[17] Griffiths K L, Stylianou E, Poyntz H C, Betts G J, Fletcher H A, McShane H. Cholera toxin enhances vaccine-induced protection against *Mycobacterium tuberculosis* challenge in mice. PLoS One. 2013; 8:e78312.
[18] Slight S R, Rangel-Moreno J, Gopal R, Lin Y, Fallert Junecko B A, Mehra S, et al. CXCR5(+) T helper cells mediate protective immunity against tuberculosis. J Clin Invest. 2013; 123:712-26.
[19] Griffiths K L, Ahmed M, Das S, Gopal R, Horne W, Connell T D, et al. Targeting dendritic cells to accelerate T-cell activation overcomes a bottleneck in tuberculosis vaccine efficacy. Nat Commun. 2016; 7:13894.
[20] Mutsch M, Zhou W, Rhodes P, Bopp M, Chen R T, Linder T, et al. Use of the inactivated intranasal influenza vaccine and the risk of Bell's palsy in Switzerland. N Engl J Med. 2004; 350:896-903.
[21] Stanberry L R, Simon J K, Johnson C, Robinson P L, Morry J, Flack M R, et al. Safety and immunogenicity of a novel nanoemulsion mucosal adjuvant W805EC combined with approved seasonal influenza antigens. Vaccine. 2012; 30:307-16.
[22] Bielinska A U, Gerber M, Blanco L P, Makidon P E, Janczak K W, Beer M, et al. Induction of Th17 cellular immunity with a novel nanoemulsion adjuvant. Crit Rev Immunol. 2010; 30:189-99.
[23] Gopal R, Lin Y, Obermajer N, Slight S, Nuthalapati N, Ahmed M, et al. IL-23-dependent IL-17 drives Th1-cell responses following *Mycobacterium bovis* BCG vaccination. Eur J Immunol. 2012; 42:364-73.
[24] Nakae S, Komiyama Y, Nambu A, Sudo K, (wase M, Homma I, et al. Antigen-specific T cell sensitization is impaired in IL-17-deficient mice, causing suppression of allergic cellular and humoral responses. Immunity. 2002; 17:375-87.
[25] Datta S K, Sabet M, Nguyen K P, Valdez P A, Gonzalez-Navajas J M, Islam S, et al. Mucosal adjuvant activity of cholera toxin requires Th17 cells and protects against inhalation anthrax. Proc Natl Acad Sci USA. 2010; 107:10638-43.
[26] Lee J B, Jang J E, Song M K, Chang J. Intranasal delivery of cholera toxin induces th17-dominated T-cell response to bystander antigens. PLoS One. 2009; 4:e5190.
[27] Ahmed M, Jiao H, Domingo-Gonzalez R, Das S, Griffiths K L, Rangel-Moreno J, et al. Rationalized design of a mucosal vaccine protects against *Mycobacterium tuberculosis* challenge in mice. J Leukoc Biol. 2017.
[28] Carter D, Reed S G. Role of adjuvants in modeling the immune response. Curr Opin HIV AIDS. 2010; 5:409-13.
[29] El-Kamary S S, Pasetti M F, Mendelman P M, Frey S E, Bernstein D I, Treanor J J, et al. Adjuvanted intranasal Norwalk virus-like particle vaccine elicits antibodies and antibody-secreting cells that express homing receptors for mucosal and peripheral lymphoid tissues. J Infect Dis. 2010; 202:1649-58.
[30] Mills K H, Cosgrove C, McNeela E A, Sexton A, Giemza R, Jabbal-Gill I, et al. Protective levels of diphtheria-neutralizing antibody induced in healthy volunteers by unilateral priming-boosting intranasal immunization associated with restricted ipsilateral mucosal secretory immunoglobulin a. Infect Immun. 2003; 71:726-32.

[31] Chatterjee S, Dwivedi V P, Singh Y, Siddiqui I, Sharma P, Van Kaer L, et al. Early secreted antigen ESAT-6 of *Mycobacterium tuberculosis* promotes protective T helper 17 cell responses in a toll-like receptor-2-dependent manner. PLoS Pathog. 2011; 7:e1002378.

[32] Saunders B M, Cooper A M. Restraining mycobacteria: role of granulomas in mycobacterial infections. Immunol Cell Biol. 2000; 78:334-41.

[33] Khader S A, Guglani L, Rangel-Moreno J, Gopal R, Junecko B A, Fountain J J, et al. IL-23 is required for long-term control of *Mycobacterium tuberculosis* and B cell follicle formation in the infected lung. J Immunol. 2011; 187:5402-7.

[34] Khader S A, Rangel-Moreno J, Fountain J J, Martino C A, Reiley W W, Pearl J E, et al. In a murine tuberculosis model, the absence of homeostatic chemokines delays granuloma formation and protective immunity. J Immunol. 2009; 183:8004-14.

[35] Rangel-Moreno J, Carragher D M, de la Luz Garcia-Hernandez M, Hwang J Y, Kusser K, Hartson L, et al. The development of inducible bronchus-associated lymphoid tissue depends on IL-17. Nat Immunol. 2011; 12:639-46.

[36] Rangel-Moreno J, Moyron-Quiroz J E, Hartson L, Kusser K, Randall T D. Pulmonary expression of CXC chemokine ligand 13, CC chemokine ligand 19, and CC chemokine ligand 21 is essential for local immunity to influenza. Proc Natl Acad Sci USA. 2007; 104:10577-82.

[37] Malley R, Srivastava A, Lipsitch M, Thompson C M, Watkins C, Tzianabos A, et al. Antibody-independent, interleukin-17A-mediated, cross-serotype immunity to pneumococci in mice immunized intranasally with the cell wall polysaccharide. Infect Immun. 2006; 74:2187-95.

[38] Zhang Z, Clarke T B, Weiser J N. Cellular effectors mediating Th17-dependent clearance of pneumococcal colonization in mice. J Clin Invest. 2009; 119:1899-909.

[39] Banus S, Stenger R M, Gremmer E R, Dormans J A, Mooi F R, Kimman T G, et al. The role of Toll-like receptor-4 in pertussis vaccine-induced immunity. BMC Immunol. 2008; 9:21.

[40] Higgins S C, Jarnicki A G, Lavelle E C, Mills K H. TLR4 mediates vaccine-induced protective cellular immunity to *Bordetella pertussis*: role of IL-17-producing T cells. J Immunol. 2006; 177:7980-9.

[41] Chen K, McAleer J P, Lin Y, Paterson D L, Zheng M, Alcorn J F, et al. Th17 cells mediate Glade-specific, serotype-independent mucosal immunity. Immunity. 2011; 35:997-1009.

[42] Priebe G P, Walsh R L, Cederroth T A, Kamei A, Coutinho-Sledge Y S, Goldberg J B, et al. IL-17 is a critical component of vaccine-induced protection against lung infection by lipopolysaccharide-heterologous strains of *Pseudomonas aeruginosa*. J Immunol. 2008; 181: 4965-75.

[43] Dye, C. The potential impact of new diagnostic tests on tuberculosis epidemics. Indian J Med Res 135, 737-744 (2012).

[44] Dye, C. & Williams, B. G. The population dynamics and control of tuberculosis. Science 328, 856-861 (2010).

[45] Griffiths, K. L. & Khader, S. A. Novel vaccine approaches for protection against intracellular pathogens. Curr Opin Immunol 28, 58-63 (2014).

[46] Khader, S. A., et al. IL-23 and IL-17 in the establishment of protective pulmonary CD4+ T cell responses after vaccination and during *Mycobacterium tuberculosis* challenge. Nat Immunol 8, 369-377 (2007).

[47] Gopal, R., et al. Interleukin-17-dependent CXCL13 mediates mucosal vaccine-induced immunity against tuberculosis. Mucosal immunology 6, 972-984 (2013).

[48] Aguilo, N., et al. Pulmonary but Not Subcutaneous Delivery of BCG Vaccine Confers Protection to Tuberculosis-Susceptible Mice by an Interleukin 17-Dependent Mechanism. J Infect Dis (2015).

[49] Monin, L., et al. Immune requirements for protective Th17 recall responses to *Mycobacterium tuberculosis* challenge. Mucosal immunology (2015).

[50] Aagaard, C., et al. A multistage tuberculosis vaccine that confers efficient protection before and after exposure. Nature medicine 17, 189-194(2011).

[51] Bertholet, S., et al. A defined tuberculosis vaccine candidate boosts BCG and protects against multidrug-resistant Mycobacteriumtuberculosis. Science translational medicine 2, 53ra74 (2010).

[52] Goonetilleke, N. P., et al. Enhanced immunogenicity and protectiveefficacy against *Mycobacterium tuberculosis* of bacille Calmette-Guerin vaccine using mucosal administration and boosting with a recombinant modified vaccinia virus Ankara. Journal of immunology 171, 1602-1609 (2003).

[53] Tchilian, E. Z., et al. Immunogenicity and protective efficacy of prime-boost regimens with recombinant (delta)ureC hly+*Mycobacterium bovis* BCG and modified vaccinia virus ankara expressing *M. tuberculosis* antigen 85A against murine tuberculosis. Infection and immunity 77, 622-631 (2009).

[54] Sweeney, K. A., et al. A recombinant *Mycobacterium smegmatis*induces potent bactericidal immunity against *Mycobacterium tuberculosis*. Nature medicine 17, 1261-1268 (2011).

[55] Grode, L., et al. Increased vaccine efficacy against tuberculosis of recombinant *Mycobacterium bovis* bacille Calmette-Guerin mutants that secret listeriolysin. The Journal of clinical investigation 115, 2472-2479 (2005).

[56] Martin, C., et al. The live *Mycobacterium tuberculosis* phoP mutant strain is more attenuated than BCG and confers protective immunity against tuberculosis in mice and guinea pigs. Vaccine 24, 3408-3419 (2006).

[57] Marcus, S. A., Steinberg, H. & Talaat, A. M. Protection by novel vaccine candidates, *Mycobacterium tuberculosis* DeltamosR and DeltaechA7, against challenge with a *Mycobacterium tuberculosis* Beijing strain. Vaccine (2015).

[58] Kaushal, D., et al. Mucosal vaccination with attenuated *Mycobacterium tuberculosis* induces strong central memory responses and protects against tuberculosis. Nature communications 6, 8533 (2015).

[59] Harding, C. V. & Boom, W. H. Regulation of antigen presentation by *Mycobacterium tuberculosis*: a role for Toll-like receptors. Nature reviews. Microbiology 8, 296-307 (2010).

[60] Reiley, W. W., et al. ESAT-6-specific CD4 T cell responses to aerosol *Mycobacterium tuberculosis* infection are initiated in the mediastinal lymph nodes. Proceedings of the National Academy of Sciences of the United States of America 105, 10961-10966 (2008).

[61] Wolf, A. J., et al. Initiation of the adaptive immune response to *Mycobacterium tuberculosis* depends on antigen production in the local lymphnode, not the lungs. J Exp Med 205, 105-115 (2008).

[62] K. Griffiths, M. A., S. Das, R. Gopal, W. Horne, T. D. Connell, K. D. Moynihan, J. K. Kolls, D. J. Irvine, M. N. Artyomov, J. Rangel-Moreno, S. A. Khader. Targeting Dendritic Cells to accelerate T cell activation overcomes a bottleneck in tuberculosis vaccine efficacy Nature communications (In press).

What is claimed is:

1. A method of treating or preventing a *Mycobacterium* infection in a subject in need thereof, the method comprising administering intranasally to the subject a composition comprising:
   (a) a nanoemulsion comprising:
     (i) droplets having an average diameter of less than about 1,000 nm;
     (ii) an aqueous phase;
     (iii) about 1% to about 80% (v/v) of at least one oil;
     (iv) about 0.001% to about 10% (v/v) of at least one surfactant;
     (v) about 0.01% to about 50% (v/v) of at least one solvent;
     (vi) less than about 5% (v/v) of at least one quaternary ammonium compound;
   (b) at least one isolated mycobacterial antigen, or an antigenic fragment thereof; and
   wherein the subject has been subcutaneously administered a tuberculosis vaccine, and wherein administration of the composition is concurrent with or within 3 weeks after the subcutaneously administered tuberculosis vaccine.

2. The method of claim 1, wherein the at least one isolated mycobacterial antigen, or an antigenic fragment thereof is selected from *Mycobacterium tuberculosis*, thereby treating or preventing a tuberculosis infection.

3. The method of claim 1, wherein the at least one isolated antigen is selected from the group consisting of ESAT-6, CFP10, Ag85B, Hsp16.3, MTB32A, MTB39A, RV2660c, Ag85A, Ag85B, Ag85C, Rv1733cΔ/Rv2626c/rpfD ETC, and combinations thereof.

4. The method of claim 1, wherein the at least one oil is selected from the group consisting of soybean, avocado, squalene, olive, canola, corn, rapeseed, safflower, sunflower, fish and other plant oil.

5. The method of claim 1, wherein the at least one surfactant is selected from the group consisting of polysorbate 80 and polysorbate 20.

6. The method of claim 1, wherein the at least one solvent is an alcohol.

7. The method of claim 1, wherein the at least one quaternary ammonium compound is cetylpyridinum chloride (CPC).

8. The method of claim 1, wherein the isolated antigen, or an antigenic fragment thereof is present in an amount of from about 10 µg to about 50 µg.

9. The method of claim 1, wherein the isolated antigen, or an antigenic fragment thereof is present in an amount of about 25 µg.

10. The method of claim 1, wherein the isolated antigen, or an antigenic fragment thereof is ESAT-6 and Ag85B.

11. The method of any one of claims 1 to 10, wherein the droplets have an average diameter of less than 700 nm.

12. The method of any one of claims 1 to 10, wherein the droplets have an average diameter of about 400 nm.

13. The method of any one of claims 1 to 10, wherein the composition is sequentially administered with *Mycobacterium bovis* bacille Calmette-Guérin (BCG).

14. The method of any one of claims 1 to 10, wherein the composition is concurrently administered with *Mycobacterium bovis* bacille Calmette-Guérin (BCG).

15. The method of any one of claims 1 to 10, wherein the composition is formulated into a dosage form selected from the group consisting of a liquid dispersion, gel, aerosol, nasal aerosol, ointment, cream, semi-solid dose forms, and suspensions.

16. The method of any one of claims 1 to 10, wherein the composition is formulated into a nasal aerosol.

17. The method of any one of claims 1 to 10, wherein the composition is a modified release formulation.

\* \* \* \* \*

SEQUENCE LISTING

```
<160> NUMBER OF SEQ ID NOS: 2

<210> SEQ ID NO 1
<211> LENGTH: 20
<212> TYPE: PRT
<213> ORGANISM: Artificial Sequence
<220> FEATURE:
<223> OTHER INFORMATION: SYNTHESIZED

<400> SEQUENCE: 1

Thr Cys Cys Ala Thr Gly Ala Cys Gly Thr Thr Cys Cys Thr Gly Ala
1               5                   10                  15

Cys Gly Thr Thr
            20

<210> SEQ ID NO 2
<211> LENGTH: 22
<212> TYPE: PRT
<213> ORGANISM: Artificial Sequence
<220> FEATURE:
<223> OTHER INFORMATION: SYNTHESIZED

<400> SEQUENCE: 2

Gly Gly Thr Cys Cys Ala Thr Gly Ala Cys Gly Thr Thr Cys Cys Thr
1               5                   10                  15

Gly Ala Cys Gly Thr Thr
            20
```